(12) United States Patent
Demuth et al.

(10) Patent No.: US 7,368,421 B2
(45) Date of Patent: May 6, 2008

(54) USE OF DIPEPTIDYL PEPTIDASE IV INHIBITORS IN THE TREATMENT OF MULTIPLE SCLEROSIS

(75) Inventors: Hans-Ulrich Demuth, Halle/Saale (DE); Torsten Hoffmann, Halle/Saale (DE); Konrad Glund, Halle/Saale (DE); Ulrich Heiser, Halle/Saale (DE); Stephan von Hoersten, Wedemark (DE)

(73) Assignee: Probiodrug AG, Halle/Saale (DE)

( * ) Notice: Subject to any disclaimer, the term of this patent is extended or adjusted under 35 U.S.C. 154(b) by 121 days.

(21) Appl. No.: 10/126,374

(22) Filed: Apr. 19, 2002

(65) Prior Publication Data

US 2003/0119750 A1 Jun. 26, 2003

Related U.S. Application Data

(60) Provisional application No. 60/301,158, filed on Jun. 27, 2001, provisional application No. 60/360,909, filed on Feb. 28, 2002, provisional application No. 60/340,151, filed on Dec. 14, 2001, provisional application No. 60/340,182, filed on Dec. 14, 2001.

(30) Foreign Application Priority Data

| Jun. 27, 2001 | (EP) | ................................... 01114796 |
| Oct. 12, 2001 | (DE) | ................................ 101 50 203 |
| Nov. 9, 2001 | (DE) | ................................ 101 54 689 |

(51) Int. Cl.
| A61K 38/00 | (2006.01) |
| A61K 38/02 | (2006.01) |
| A61K 38/05 | (2006.01) |
| A61K 38/06 | (2006.01) |
| A61K 38/07 | (2006.01) |
| A61K 38/08 | (2006.01) |
| C07K 2/00 | (2006.01) |
| C07K 7/04 | (2006.01) |
| C07K 5/02 | (2006.01) |
| C07K 5/08 | (2006.01) |
| C07K 5/10 | (2006.01) |

(52) U.S. Cl. .............................. 514/2; 514/17; 514/18; 514/19; 530/300; 530/329; 530/330; 530/331; 530/332

(58) Field of Classification Search ..................... 514/2; 530/300, 330, 332
See application file for complete search history.

(56) References Cited

U.S. PATENT DOCUMENTS

| 2,961,377 A | 11/1960 | Shapiro et al. ................ 167/65 |
| 3,174,901 A | 3/1965 | Sterne .......................... 167/65 |
| 3,879,541 A | 4/1975 | Kabbe et al. ................ 424/326 |
| 3,960,949 A | 6/1976 | Ahrens et al. .......... 260/564 B |
| 4,028,402 A | 6/1977 | Fischer et al. .......... 260/501.14 |
| 4,935,493 A | 6/1990 | Bachovchin et al. ....... 530/331 |
| 5,433,955 A | 7/1995 | Bredehorst et al. ........ 424/94.3 |
| 5,462,928 A | 10/1995 | Bachovchin et al. ......... 514/19 |
| 5,512,549 A | 4/1996 | Chen et al. .................... 514/12 |
| 5,543,396 A | 8/1996 | Powers et al. ................ 514/19 |
| 5,614,379 A | 3/1997 | MacKellar ................ 435/68.1 |
| 5,624,894 A | 4/1997 | Bodor ........................... 514/2 |
| 5,705,483 A | 1/1998 | Galloway et al. ............. 514/12 |
| 5,827,898 A | 10/1998 | Khandwala et al. ........ 514/734 |
| 5,939,560 A * | 8/1999 | Jenkins et al. ............. 548/535 |
| 6,006,753 A | 12/1999 | Efendic ...................... 128/898 |
| 6,011,155 A | 1/2000 | Villhauer .................... 544/333 |
| 6,107,317 A | 8/2000 | Villhauer .................... 514/365 |
| 6,110,949 A | 8/2000 | Villhauer .................... 514/365 |
| 6,124,305 A | 9/2000 | Villhauer .................... 514/272 |
| 6,172,081 B1 | 1/2001 | Damon ........................ 514/307 |
| 6,201,132 B1 | 3/2001 | Jenkins et al. ............. 548/535 |
| 6,271,231 B1 * | 8/2001 | Bergstrand et al. ......... 514/249 |
| 6,303,661 B1 | 10/2001 | Demuth et al. ............. 514/866 |
| 6,319,893 B1 | 11/2001 | Demuth et al. ................ 514/2 |
| 6,500,804 B2 | 12/2002 | Demuth et al. ............... 514/19 |
| 6,526,083 B1 * | 2/2003 | Kneissl et al. ........... 372/50.22 |
| 6,548,481 B1 | 4/2003 | Demuth et al. ............... 514/19 |
| 6,586,403 B1 * | 7/2003 | Mathison et al. ............. 514/18 |
| 6,605,589 B1 | 8/2003 | Uckun et al. .................. 514/2 |
| 2001/0025023 A1 | 9/2001 | Carr .............................. 514/2 |

(Continued)

FOREIGN PATENT DOCUMENTS

DE  25 42 598 A1  4/1976

(Continued)

OTHER PUBLICATIONS

Ba 't Hart, et al. Evaluating the validity of animal models for research into therapies for immune-based disorders. (2004) Drug Discovery Today, 9, 517-524.*

(Continued)

*Primary Examiner*—Andrew D. Kosar
(74) *Attorney, Agent, or Firm*—Sonnenschein Nath & Rosenthal LLP

(57) ABSTRACT

The present invention provides a new use of DP IV-inhibitors. The compounds of the present invention, and their corresponding pharmaceutically acceptable acid addition salt forms, are useful in treating conditions mediated by DP IV or DP IV-like enzymes, such as immune, autoimmune or central nervous system disorder selected from the group consisting of strokes, tumors, ischemia, Parkinson's disease and migraines. In a more preferred embodiment, the compounds of the present invention are useful for the treatment of multiple sclerosis.

13 Claims, 4 Drawing Sheets

U.S. PATENT DOCUMENTS

2002/0165164 A1* 11/2002 Demuth et al. ............... 514/14

FOREIGN PATENT DOCUMENTS

| | | |
|---|---|---|
| DE | 296 075 A5 | 11/1991 |
| DE | 196 16 486 C2 | 10/1997 |
| DE | 299 09 210 U | 9/1999 |
| DE | 198 26 972 A1 | 12/1999 |
| DE | 198 34 610 A1 | 2/2000 |
| EP | 0 658 568 A1 | 6/1995 |
| EP | 0 708 179 A2 | 4/1996 |
| EP | 0 995 440 A1 | 4/2000 |
| EP | PCT/EP00/08118 * | 3/2001 |
| EP | 1 130 022 A1 | 9/2001 |
| FR | 2 085 665 | 12/1971 |
| FR | 2 696 740 A1 | 4/1994 |
| JP | 04-288098 | 10/1992 |
| JP | 4334357 | 11/1992 |
| WO | WO 91/11457 | 8/1991 |
| WO | WO 91/16339 | 10/1991 |
| WO | WO 91/17767 | 11/1991 |
| WO | WO 93/08259 | 4/1993 |
| WO | WO 95/11689 | 5/1995 |
| WO | WO 95/15309 | 6/1995 |
| WO | WO 95/29691 | 11/1995 |
| WO | WO 97/40832 | 11/1997 |
| WO | WO 97/45117 | 12/1997 |
| WO | WO 98/19998 | 5/1998 |
| WO | WO 98/22494 | 5/1998 |
| WO | WO 99/46272 A | 9/1999 |
| WO | WO 99/61431 | 12/1999 |
| WO | WO 99/62914 | 12/1999 |
| WO | WO 00/01849 | 1/2000 |
| WO | WO 00/10549 | 3/2000 |
| WO | WO 00/53171 | 9/2000 |
| WO | WO 01/09169 A2 | 2/2001 |
| WO | WO 01/32624 A1 | 5/2001 |
| WO | WO 01/34594 A1 | 5/2001 |
| WO | WO 01/62266 A2 | 8/2001 |
| WO | WO 01/74299 A2 | 10/2001 |
| WO | WO 01/89569 A1 | 11/2001 |
| WO | WO 01/94310 A1 | 12/2001 |
| WO | WO 01/97808 | 12/2001 |
| WO | WO 2004/066931 A2 | 12/2001 |
| WO | WO 02/20825 A1 | 3/2002 |
| WO | WO 03/016335 A2 | 2/2003 |

OTHER PUBLICATIONS

A Sedo and R Malik. Dipeptidyl peptidase IV-like molecules: homologous protein or homologous activities? (2001) Biochmica et Biophysica Acta, 1550, 107-116.*
W.S. Messer, "Vasopressin and Oxytocin", web document updated Apr. 3, 2000; http://www.neurosci.pharm.utoledo.edu/MBC3320/Vasopressin.htm; 5 pages.*
D. Voet and J.G. Voet. Biochemistry, 2nd Edition.(1995), pp. 235-241.*
J. Rudinger. In: Peptide Hormones, JA Parsons, Ed. (1976) 1-7.*
D.E. Smilek, et al. Proc. Natl. Acad. Sci. USA (1991) 88, pp. 9633-9637.*
Ba 't Hart, et al. Drug Discovery Today (2004) 9, 517-524.*
A Sedo and R Malik. Biochimica et Biophysica Acta (2001) 1550, 107-116.*
I. De Meester, et al. Immunol. Today (1999) 20(8), pp. 367-375.*
A. Steinbrecher, et al. Adv. Exp. Med. Biol. (2000) 477, pp. 145-153.*
D. Reinhold, et al. Adv. Exp. Med. Biol. (2000) 477, pp. 155-160.*
"Progress Continues Against Multiple Sclerosis." Mercy Health System of Oklahoma. Mar. 2005, 4 pages, internet document <<http://www.mercyok.net/healthinfo/archive/050330.asp>>, accessed Oct. 10, 2006.*

Campbell, I.W. New Antidiabetic Drugs, ed. C.J. Bailey & P.R. Flatt, Smith-Gordon, "Sulphonylureas and metformin: efficacy and inadequacy". 3:33-51 (1990).
The Merck Index, 11th Edition, An Encyclopedia of Chemicals, Drugs, and Biologicals, 1996, p. 934.
The Merck Index, 12th Edition, An Encyclopedia of Chemicals, Drugs, and Biologicals, 1996, p. 1014.
Martindale The Extra Pharmacopoeia, 30th Edition, London Pharmaceutical Press, 1993, p. 1619.
Martindale The Extra Pharmacopoeia, 30th Edition, London Pharmaceutical Press, 1993, p. 36.
Chemical Abstracts, vol. 115. No. 15, Oct. 14, 1991 Columbus, Ohio, US; abstract No. 149947q, Schoen Ekkehard et al: "Dipeptidyl peptidase IV in the immune system. Effects of specific enzyme inhibitors on activity of dipeptidyl peptidase IV and proliferation of human lymphocytes".
Chemical Abstracts, vol. 126, No. 2, Jan. 13, 1997 Columbus, Ohio, US; abstract No. 16161j, Stoeckel A. et al: "Competitive inhibition of proline specific enzymes by amino acid thioxopyrrolidides and thiazolidides".
Chemical Abstracts, vol. 118, No. 25, Jun. 21, 1993 Columbus, Ohio, US; abstract No. 255342k, Hosoda, et al, "Preparation of N-(heterocyclic Carbonyl) Amino Acids and Analogs as Prolyl Endopeptidase Inhibitors", Nov. 1992.
Arai et al: "Synthesis of prolyl endopeptidase inhibitors and evaluation of their structure-activity relationships : in vitro inhibition of prolyl endopeptidase from Canine Brain" Chemical and Pharmaceutical Bulletin., Bd. 41, No. 9, 1993, pp. 1583-1588.
J. Lin et al.: "Inhibition of depeptidyl peptidase IV by fluoroolefin-containing n-peptidyl-O-hydroxylamine peptidomimetics" Proceedings of the National Academy of Sciences of USA, vol. 95, Nov. 1998, pp. 14020-14024.
Korom, S., et al "Inhibition of CD26/dipeptidyl peptidase IV activity in vivo prolongs cardiac allograft survival in rat recipients", Transplantation vol. 63, 1495—1500 No. 10 (1997).
Tanka, S., et al., "Suppression of arthritis by the inhibitors of dipeptidyl peptidase IV". Int. J. Immunopharmacol, vol. 19, No. 1 pp. 15-24, 1997.
Mentlein, R., et al., "Proteolytic processing of neuropeptide Y and peptide YY by dipeptidyl peptidase IV". Regul. Pept. 49, 133-144(1993).
Wetzl, W., et al., "Effects of the CLIP fragment ACTH 20-24 on the duration of REM sleep episodes". Neuropeptides, 31, 41-45 (1997).
Amasheh, S., et al., "Electrophysiological analysis of the function of the mammalian renal peptide transporter expressed in *Xenopus laevis* oocytes". J. Physiol. 504, 169-174 (1997).
Durinx, C.; et al.; "Reference Values for Plasma Dipeptidyl-Pepidase IV activity and their Associatin with Other Laboratory Parameters". Clin Chem Lab Med 2001, February; 39 (2) : 155-9, 1 page.
Gossrau, R.; "Cytochemistry of Membrane Proteases". Histochem J, Jul. 1985; 17 (7) :737-71, 1 page, Abstract only.
Hahn, T.; et al.; "Enzyme Histochemical Evidence for the Presence of Potential Blood Pressure Regulating Proteases in Cultured Villous Explants from Human First Trimester Placentae". Acta Histochem 1993, Dec. 1995 (2) :185-92, 1 page.
Heymann, E.; et al.; "Has Dipeptidyl Peptidase IV an Effect on Blood Pressure and Coagulation." Klin Wochenschr, Jan. 2, 1984;62 (1) :2-10, 1 page.
Magyar, C.E.; et al.; "Proximal Tubule Na Transporter Responses are the same during Acute and Chronic Hypertension." Am J Physiol Renal Physiol, Aug. 2000; 279 (2) :F358-69, 1 page.
Papies, B.; et al.; "Isoenzyme (Lactate Dehydrogenase, Aspartate Aminotransferase) and Dipeptidyl Peptidase IV Activity Changes in Blood Plasma Likely Indicative of Organ Involvement due to Arterial Hypertension." Cor Vasa, 1991; 33 (3) :218-26, 1 page.
Qureshi. N.U.; et al., "Endogenous Neuropeptide Y Mediates Vasoconstriction during Endotoxic and Hemorrhagic Shock". Regul Pept, Sep. 25, 1998; 75-76:215-20, 1 page.
Index Nominum, International Drug Directory 1992/1993, Medpharm Scientific Publishers, pp. 728-729.
The Merck Index, An Encyclopedia of Chemicals and Drugs, 9th Edition, Merck & Co., Inc., 1976, p. 773.

The Merck Index, An Encyclopedia of Chemicals and Drugs, 9th Edition, Merck & Co., Inc., 1976, p. 5794.

C.J. Bailey et al., *New Antidiabetic Drugs*, Smith-Gordon Nishimura, 1990, p. 36.

Willms et al., *Journal of Clinical Endocrinology Metabolism*, "Gastric Emptying, Glucose Responses, and Insulin Secretion after a Liquid Test Meal: Effects of Exogenous Glucagon-Like Peptide-1 (GLP-1)-(7-36) Amide in Type 2 (Noninsulin-Dependent) Diabetic Patients", 1996, 81(1):327-332.

Hoffmann et al., *Journal of Chromatography A*, "Inhibition of dipeptidyl peptidase IV (DP IV) by anti-DP IV antibodies and non-substrate X-X-Pro- oligopeptides ascertained by capillary eletrophoresis", 1995, 716:355-362.

C.B. Welch, *Medical Management of Non-Insulin-Dependent (Type II) Diabetes*, 3rd edition, American Diabetes Association, "Diagnosis and Classification" p. 3, 1994, Pharmacologic Intervention (1 page).

Mannucci et al., *Diabetes Care*, "Effect of Metformin on Glucagon-Like Peptide 1 (GLP-1) and Leptin Levels in Obese Nondiabetic Subjects", 24(3): 489-494, Mar. 2001.

Stryer, *Biochemistry 3rd Ed.*, "Protein Conformation, Dynamics, and Function", 1988, p. 191-193.

Pauly et al., *Regulatory Peptides*, "Abstracts Issue: Abstracts from the 11th International Symposium on Regulatory Peptides", Jul. 15, 1996, 64(1-3): 148 plus cover.

Gutniak et al., *New England Journal of Medicine*, "Antidiabetogenic Effect of Glucagon-like peptide-1 (7-36) Amide in Normal Subjects and Patients With Diabetes Mellitus", 1992, 326: 1316-1322.

Hendrick et al., *Metabolism, Metabolism—Clinical and Experimental*, "Glucagon-like Peptide-1-(7-37) Suppresses Hyperglycemia in Rats", Jan. 1993, 42(1): 1-6.

Nauck et al., *Diabetologia*, "Normalization of fasting hyperglycaemia by exogenous glucagon-like peptide 1 (7-36 amide) in Type 2 (non-insulin-dependent) diabetic patients",1993, 36: 741-744.

Gutniak et al., *Diabetes Care*, "Subcutaneous Injection of the Incretin Hormone Glucagon-Like Peptide 1 Abolishes Postprandial Glycemia in NIDDM", Sep. 1994, 17(9): 1039-1044.

Deacon et al., *Journal of Clinical Endocrinology and Metabolism*, "Degradation of Glucagon-Like Peptide-1 by Human Plasma in Vitro Yields and N-Terminally Truncated Peptide That Is a Major Endogenous Metabolite in Vivo", 1995, 80(3): 952-957.

H.A. Smith et al., *Veterinary Pathology* (fourth edition), "Diseases and Disorders of Metabolism: Deficiency Disease", 1972, p. 1018-1020.

G.G. Duncan, *Diseases of Metabolism (Asian edition)*, "Diabetes Aellitus", 1966, p. 951-957.

T.J. Kieffer et al.; "Degradation of Glucose-Dependent Insulinotropic Polypetide and Truncated Glucagon-Like Peptide 1 In Vitro and In Vivo by DP IV", Endocrinology, vol. 136(8), 1995, p. 3585-3596.

C.F. Deacon et al., *Diabetes*, "Both Subcutaneously and Intravenously Administered Glucagon-Like Peptide I Are Rapidly Degraded from the $NH_2$-Terminus in Type II Diabetic Patients and in Healthy Subjects", Sep. 1995, 44: 1126-1131.

R. Mentlein et al., *European Journal of Biochemistry*, "Dipeptidyl-Peptidase IV Hydrolyses Gastric Inhibitory Polypeptide, Glucagon-Like Peptide-1 (7-36) Amide, Peptide Histidine Methionine and is Responsible for their Degradation in Human Serum", vol. 214, 1993, p. 829-835.

Pauly et al., *Metabolism*, "Improved Glucose Tolerance in Rats Treated with the Dipeptidyl Peptidase IV (CD26) Inhibitor Ile-Thiazolidide", 1999, 48(3): 385-389.

*Goodman & Gilman's The Pharmacological Basis of Therapeutics*, Ninth Edition, 1996, p. 1510.

Nathan et al., *Diabetes Care*, "Insulinotropic Action of Glucagon-like Peptide-1-(7-37) in Diabetic and Nondiabetic Subjects", Feb. 1992, 15(2): 270-275.

Frohman et al.,*Journal of Clin. Invest.*, "Rapid Enzymatic Degradation of Growth Hormone-releasing Hormone by Plasma in Vitro and in Vivo to a Biologically Inactive Product Cleaved at the $NH_2$ Terminus", vol. 78, Oct. 1986, p. 906-913.

Snow et al., *Advances In Medicinal Chemistry*, "Boronic Acid Inhibitors of Dipeptidyl Peptidase IV: A New Class of Immunosuppressive Agents", vol. 3, 1995, p. 149-177.

Thorens et al., *Diabetes*, "Glucagon-Like Pepetide-I and the Control of Insulin Secretion in the Normal State and in NIDDM", 1993, 42:1219-1225.

Wakselman et al., "Inhibition of HIV-1 infection of CD $26^+$but not CD 26 cells by a potent cyclopeptidic inhibitor of the DPP IV activity of CD26", Abstract P 44 of the 24th European Peptide Symposium, 1996.

Ashworth et al., *Bioorg. Med. Chem. Lett.*, "2-Cyanopyrrolidides as Potent, Stable Inhibitors of Dipeptidyl Peptidase IV", 1996, 6(10): 1163-1166.

Endroczi et al., *Acta Physiol. Hung.*, "Dipeptidyl peptidase IV (DP IV) and Superoxide Dismutase Activity in Thymus-Derived Lymphocytes: Effects of Inhibitory Pepdides and $Zn^{2+}$in Vitro", 1990, 75(1): 35-44.

Lee, H.S. et al., "Cathepsin B Inhibitory Peptides Derived from -Casein," Peptides 21 (2000) 807-809.

Edwards, J.V. et al., *J. Peptide Res.*, "Synthesis and Activity of $NH_2$—and COOH-Terminal Elastase Recognition Sequences on Cotton," 1999, 54: 536-543.

Wettstein, J.G. et al. *Pharmacology & Therapeutics*, "Central Nervous System Pharmacology of Neuropeptide Y.", (1995), 65(3): 397-414.

Bergmeier, Stephen C., *Tetrahedron, Elsevier Science Ltd.*, "The Synthesis of Vicinal Amino Alcohols", vol. 56, No. 17, (2000), pp. 2561-2576.

Kawamoto et al., *Tetrahedron Asymmetry, Elsevier Science Ltd.*, "Enantioselective Synthesis of β-Hydroxy Amines and Aziridines Using Asymmetric Transfer Hydrogenation of α-Amido Ketones", vol. 11, No. 16 (2000), pp. 3257-3261.

Orskov, Cathrine et al., "Proglucagon Products in Plasma of Noninsulin-dependent Diabetics and Nondiabetic Controls in the Fasting State and after Oral Glucose and Intravenous Arginine" *J. Clin. Invest.*, vol. 87, 1991, pp. 415-423.

Sengupta, et al., *Tetrahedron Letters, Elsevier Science Ltd.* "Amino Acid Derived Morpholine Amides for Nucleophilic α-Amino Acylation Reactions: A New Synthetic Route to Enantiopure α-Amino Ketones", vol. 40, No. 21 (1999), pp. 4107-4110.

Stryer, Lubert, *Biochemistry*, "Amino Acid Degradation and the Urea Cycle" (1975) pp. 451-452.

Wen-Tien Chen et al. "Seprase Complexes in Cellular Invasiveness", *Cancer and Metastasis Review* 22: 259-269, (2003).

Victor A. Gault et al., "Glucose-Dependent Insulinotropic Polypeptide Analogues and Their Therapeutic Potential for the Treatment of Obesity-Diabetes", *Biochemical and Biophysical Research Communications* 308: 207-213, (2003).

Augustyns et al., *Eur. J. Med. Chem.*, "Pyrrolidides: Synthesis and Structure-Activity Relationship as Inhibitors of Dipeptidyl Peptidase IV", (1997), vol. 32, pp. 301-309.

Lader, Malcolm H., MD, "Assessment Methods and the Different Diagnosis of Anxiety", *Journal of Clinical Psychopharmacology*, (1981), vol. 1, No. 6, pp. 342-349.

Winslow, R., "Novartis Drug Alters Picture for Diabetes" *Wall Street Journal*, Wed., Dec. 27, 2000, p. B2.

Ansorge, S., et al., "Membrane-bound peptidases of lymphocytes: Functional implications", *Biomed. Biochim*, Acta 50 (1991) 4-6, pp. 799-807.

Dodge, R.W., et al., "Folding and Unfolding Kinetics of the Proline-to-Alanine Mutants of Bovine Pancreatic Ribonuclease A," *Biochemistry* 1996, 35, pp. 1548-1559.

Demuth, Hans-Ulrich, "Recent Developments in Inhibiting Cysteine and Serine Proteases", *J. Enzyme Inhibition*, 1990, vol. 3, pp. 249-278.

Gomez, S., et al., "Relationship between endo- and exopeptidases in a processing enzyme system: Activation of an endoprotease by the aminopeptidase B-like activity in somatostatin-28 convertase",*Proc. Natl. Acad. Sci. USA*, vol. 85 pp. 5468-5472, Aug. 1988.

Hegen, M., et al., "The T Cell Triggering Molecule Tp103 is Associated with Dipeptidyl Aminopeptidase IV Activity," *The Journal of Immunology*, vol. 144, pp. 2908-2914, No. 8, Apr. 15, 1990.

Ishiura, S., et al., "Identification of a putative amyloid A4-generating enzyme as a prolyl endopeptidase," *Federation of European Biochemical Societies*, vol. 260, No. 1, pp. 131-134, Jan. 1990.

Kräusslich, Hans-Georg, et al., "Viral Proteinases", *Ann. Rev. Biochem*. 1988, 57 pp. 701-754.

Pederson, R.A., et al., "improved Glucose Tolerance in Zucker Fatty Rats by Oral Administration of the Dipeptidyl Peptidase IV Inhibitor Isoleucine Thiazolidide", *Diabetes*, vol. 47, Aug. 1998 pp. 1253-1258.

Vanhoof, G., et al., "Proline motifs in peptides and their biological processing", The FASEB Journal, vol. 9, Jun. 1995, pp. 736-744.

Walter, R., et al,. "Proline Specific Endo- and Exopeptidases", *Molecular & Cellular Biochemistry*, vol. 30, No. 2, Apr. 18, 1980, pp. 111-127.

Kessler, Von Horst, "Konformation und biologische Wirkung von cyclischen Peptiden", *Angew. Chem*. 94 (1982) pp. 509-520.

Kirschke, H. et al., "Proteinases 1: Lysosomal Cysteine Proteinases" *Protein Profile*, vol. 2, Issue 14, 1995, pp. 1583-1634.

Yaron, A., et al., "Proline-Dependent Structural and Biological Properties of Peptides and Proteins" *Critical Reviews in Biochemistry and Molecular Biology*, 28(1), pp. 31-81 (1993).

Vallee et al., "Larval Development of *Tribolium confusum* in the Presence on Non-Naturally Occurring Amino Acids", Database CAPLUS on STN, Accession No. 1963:75103, *Annales de l'ACFAS* (1962), 28, p. 26-27 (abstract).

Holst, J. et al., "Inhibition of the Activity of Dipeptidyl-Peptidase IV as a Treatment for Type 2 Diabetes", *Diabetes*, 47, 11, Health & Medical Complete pp. 1663-1670, Nov. 1998.

Munglani R. et al., Drugs, *Adis International Ltd*, At, "The Therapeutic Potential of Neuropeptide Y Analgesic, Anxiolytic and Antihypertensive", (1996) 52(3): 371-389.

Reinhold, D. et al., *Journal of Neuroimmunology*, "Inhibitors of Dipeptidyl Peptidase IV/CD26 Suppress Activation of Human MBP-Specific CD4 + T Cell Clones", (1998) 87: 203-209.

Stöckel-Maschek, A., et al., *Biochimica et Biophysica Acta*, "Thioxo Amino Acid Pyrrolidides and Thiazolidides: new Inhibitors of Proline Specific Peptidases", (2000) 1479: 15-31.

Shaw, Michael K. et al. "Cysteine and Serine Protease Inhibitors Block Intracellular Development and Disrupt the Secretory Pathway of *Toxoplasma gondii*", *Microbes and Infection*, 4, pp. 119-132 (2002).

Brömme, Dieter et al., "*N*-Peptidyl-*O*-Carbamoyl Amino Acid Hydroxamates: Irreversible Inhibitors for the Study of the $S_2'$ Specificity of Cysteine Proteinases", *Federation of European Biochemical Societies Letters*, vol. 322, No. 3, pp. 211-214, (1993).

*Vidal*, 1993, 69th Edition, p. 612-613.

Pschyrembel, Kininisches Worterbuch 257, Auflage, 1994, 9 pages.

Dang, N.H., et al., "CD26: An Expanding Role in Immune Regulation and Cancer", *Histopathology/C ellular and Molecular Biology*, (2002).

Wender, Mieczyslaw et al., "The Effect of Short-Term Treatment with Interferon β 1A ON Acute Experimetnal Allergic Encephalomyelitis", *Folia Neuropathol*, vol. 39, No. 2, pp. 91-93, (2001).

News Article: "Tysabri Dominates Biogen Idex meeting Apr. 6, 2004; Possible new PML case trip Biogen Apr. 6, 2005", May 27, 2005.

News Article: "Elan Corp plc and Biogen IDEC Inc. Have Suspended marketing and Clinical Trials of Natalizumab", May 16, 2005.

Steinbrecher, et al., Targeting Dipeptidyl Peptidase IV (CD26) Suppresses Autoimmune Encephalomyelitis and Up-Regulates TGF-β1 Secretion In Vivo, The American Association of Immunologists, 2001, pp. 2041 to 2048.

Wekerle, Kojima, Lannes-Vieira, Lassmann, Linington (1995) Animal Models, Annals of Neurology 36, S47-S53.

Demuth, Heins (1995) Cat. Mech. of Dipeptidyl Peptidase IV. In: Fleischer, eds. Dipeptidyl Peptidase IV (CD26) in Metabolism and Immune Response, 1-35, RG Landes Co (1995).

Evans (2002) Dipeptidyl peptidase IV inhibitors, IDrugs 5(6), 577-588.

\* cited by examiner

USE OF DIPEPTIDYL PEPTIDASE IV INHIBITORS IN THE TREATMENT OF MULTIPLE SCLEROSIS

RELATED APPLICATIONS

This application claims the priority of U.S. provisional application U.S. 60/301,158 entitled Peptide Structures Useful for Competitive modulation of Dipeptidyl Peptidase IV Catalysis filed on Jun. 27, 2001. Priority is also claimed from U.S. provisional application 60/360,909 entitled Glutaminyl-based DP IV Inhibitors filed on Feb. 28, 2002. Priority is further claimed from U.S. provisional application U.S. 60/340,151 entitled Peptidylketones as DP IV inhibitors filed on Dec. 14, 2001 and U.S. provisional application 60/340,182 entitled Substituted Aminoketones filed on Dec. 14, 2001. This application also claims the priorty of the following foreign applications EP 01 114 796.4 entitled Peptide Structures Useful for Competitive Modulation of Dipeptidyl Peptidase IV Catalysis having a priority date of Jun. 27, 2001, DE 101 50 203.6 entitled Peptidylketone als Inhibitoren der DP IV having a priority date of Oct. 12, 2001 and DE 101 54 689.0 entitled Substituierte Aminoketonverbindungen having a priority Date of Nov. 9, 2001. The above appliations are incoporated in their entirety by reference.

FIELD OF THE INVENTION

The present invention relates to inhibitors of dipeptidyl peptidase IV and dipeptidyl peptidase IV-like enzyme activity and, more particularly, pharmaceutical compositions containing said compounds, and the use of said compounds for the treatment of central nervous disorders, immune and autoimmune disorders. The present invention especially provides a method for the treatment of multiple sclerosis.

BACKGROUND ART

Dipeptidyl peptidase IV (DP IV) is a serine protease which cleaves N-terminal dipeptides from a peptide chain containing, preferably, a proline residue in the penultimate position. Although the biological role of DP IV in mammalian systems has not been completely established, it is believed to play an important role in neuropeptide metabolism, T-cell activation, attachment of cancer cells to the endothelium and the entry of HIV into lymphoid cells.

Likewise, it has been discovered that DP IV is responsible for inactivating glucagon-like peptide-1 (GLP-1) and glucose-dependent insulinotropic peptide also known as gastric-inhibitory peptide (GIP). Since GLP-1 is a major stimulator of pancreatic insulin secretion and has direct beneficial effects on glucose disposal, in WO 97/40832 and U.S. Pat. No. 6,303,661 inhibition of DP IV and DP IV-like enzyme activity was shown to represent an attractive approach for treating non-insulin-dependent diabetes mellitus (NIDDM).

The present invention provides a new use of DP IV-inhibitors for the treatment of conditions mediated by inhibition of DP IV and DP IV-like enzymes, in particular the treatment of neuronal disorders and immune disorders including multiple sclerosis, and pharmaceutical compositions e.g. useful in inhibiting DP IV and DP IV-like enzymes and a method of inhibiting said enzyme activity.

This invention relates to a method of treatment, in particular to a method for the treatment of central nervous disorders, immune and autoimmune disorders, especially multiple sclerosis and to compositions for use in such method. Dipeptidyl peptidase IV (DP IV) is a post-proline (to a lesser extent post-alanine, post-serine or post-glycine) cleaving serine protease found in various tissues of the body including kidney, liver, and intestine.

It is known that DP IV-Inhibitors may be useful for the treatment of impaired glucose tolerance and diabetes mellitus (International Patent Application, Publication Number WO 99/61431, Pederson R A et al, Diabetes. 1998 August; 47(8):1253-8 and Pauly R P et al, Metabolism 1999 March; 48(3):385-9). In particular WO 99/61431 discloses DP IV-Inhibitors comprising an amino acid residue and a thiazolidine or pyrrolidine group, and salts thereof, especially L-threo-isoleucyl thiazolidine, L-allo-isoleucyl thiazolidine, L-threo-isoleucyl pyrrolidine, L-allo-isoleucyl thiazolidine, L-allo-isoleucyl pyrrolidine, and salts thereof.

The term DP IV-like enzymes relates to structurally and/or functionally DP IV/CD26-related enzyme proteins (Sedo & Malik, Dipeptidyl peptidase IV-like molecules: homologous proteins or homologous activities? Biochimica et Biophysica Acta 2001, 36506: 1-10). In essence, this small group of enzymes has evolved during evolution to release H-Xaa-Pro-Dipeptides and H-Xaa-Ala-Dipeptides from N-terminus of oligo- or polypeptides. They show the common feature, that they accomotate in the Pro-position also Al, Ser, Thr and other amino acids with small hydrophobic side-chains as, Gly or Val. The hydrolytic efficacy is ranked Pro>Ala>>Ser, Thr>>Gly, Val. Same proteins have been only available in such small quantities, that only the post-Pro or post-Ala cleavage could be established. While the proteins: DP IV, DP II, FAPα (Seprase), DP 6, DP 8 and DP 9 are structurally related and show a high sequence homology of, attraction is an extraordinary functional DP IV-like enzyme, characterized by a similar activity and inhibitory pattern.

Dipeptidyl peptidase IV (CD26) has to be shown an activation marker for T, B, and NK cells (Schön, E., Demuth, H. U., Barth, A., and Ansorge, S. (1984) *Biochem. J.* 223, 255-258, Bühling, F, Junker, U, Reinhold, D, Neubert, K, Jäger, L, and Ansorge, S. Functional role of CD26 on human B lymphocytes. Immunol. Lett. 45, 47-51. 1995; Ansorge, S., Schön, E., and Kunz, D. Membrane-bound peptidases of lymphocytes: functional implications. Biomed. Biochim. Acta 50, 799-807. 1991; Schön, E., Eichmann, E., Grunow, R, Jahn, S., Kiessig, S. T., Volk, H, and Ansorge, S. Dipeptidyl peptidase IV in human T lymphocytes. An approach to the role of membrane peptidases in the immune system. Biomed. Biochim. Acta 45, 1523-1528. 1986.). Surface expression of CD26 is up regulated after mitogenic, anti-CD3 or IL-2 stimulation of T cells, *S. aureus* protein stimulation of B cells and IL-2 stimulation of NK cells (Reinhold, D, Bank, U., Bühling, F, Träger, M, Born, I., Faust, J., Neubert, K., and Ansorge, S. Inhibitors of dipeptidyl peptidase IV (DP IV, CD26) induces secretion of transforming growth factor-β1 (TGF-β1) in stimulated mouse splenocytes and thymocytes. Immunol. Lett. 58, 29-35. 1997).

Stimulation of human T cells by pokeweed mitogen results in a significant increase of IL-2, IFN-γ, and DP IV mRNA expression. The changes observed in cytokine mRNA expression are dose-dependently suppressed by a specific inhibitor of dipeptidyl peptidase IV (Arndt, M., Lendeckel, U., Spiess, A, Faust, J., Neubert, K., Reinhold, D, and Ansorge, S. Dipeptidyl Peptidase IV (DP IV/CD26) mRNA Expression in PWM-Stimulated T-cells Is Suppressed by SpecificDP IV Inhibition, an Effect Mediated by TGF-β1. Biochem Biophys. Res Commun. 274, 410-414. 2000.). This effect seems to be mediated by TGF-β1.

Multiple sclerosis (MS) is a demyelinating disease of the central nervous system with a presumed autoimmune pathogenesis involving autoantigen-specific CD4+ T cells and cytokines (Rohowsky-Kochan, C, Molinaro, D, and Cook, S D. Cytokine secretion profile of myelin basic protein-specific T cells in multiple sclerosis. Multiple Sclerosis 6, 69-77. 2001.). Myelin basic protein (MBP)-specific, CD4+ T cell clones (TCC) derived from patients with multiple sclerosis express high levels of DP IV/CD26. Specific inhibition of dipeptidyl peptidase IV results in a dose-dependent suppression of DNA synthesis and IFN-γ, IL-4, and TNF-α production of the antigen-stimulated TCC (Reinhold, D, Hemmer, B, and Gran, B. Dipeptidyl peptidase IV (CD26): role in T cell activation and autoimmune disease. Adv. Exp. Med. Biol. 477, 155-160. 2000.).

Inhibitors of dipeptidyl peptidase IV suppress activation of human MBP-specific CD4+ T cell clones (Reinhold, D, Hemmer, B, Gran, B, Born, I., Faust, J., Neubert, K., McFarland, H F, Martin, R, and Ansorge, S. Inhibitors of dipeptidyl peptidase IV/CD26 suppress activation of human MBP-specific CD4+ T cell clones. J Neuroimmun 87(1-2), 203-209. 1998.).

The degeneration underlying MS results from degradation of the myelin sheath, an electrically insulating fatty layer that surrounds nerve fibers and permits the rapid conduction of electrical signals. This loss of myelin can seriously impair the ability of neurons to conduct an electrical signal effectively. Symptoms will depend on where in the central nervous system (CNS) the myelin loss occurs and, thus, which nerve pathways become impaired.

The disease appears to be autoimmune in nature, i.e., the body's own immune system is responsible for the damage. The principal target of the autoimmune reaction appears to be Myelin Basic Protein (MBP), although other MS antigens have been proposed. In the early stages of the disease, a type of CNS cell called an oligodendrocyte can repair this damage and replace the lost myelin. However, these cells can also be destroyed in MS and so sufferers may lose the ability to repair the damage over time, which allows the disease to progress.

The mechanism of disease progression appears complex and several components of the immune system have been linked to the disease. While the underlying tissue damage appears to result predominantly from a T cell mediated response, antibodies against MS antigens are often present in the cerebrospinal fluid (CSF) and at active lesions. Antibodies are not normally present in the CSF and some disruption of the blood brain barrier (BBB), a protective membrane around the CNS, must also occur to allow antibodies, T cells and macrophages to enter the CSF. This change in the permeability of the BBB appears to be one of the defining events in the development of MS.

Activated macrophages secrete pro-inflammatory cytokines such as TNF-α and interferon-γ, leading to the production of destructive enzymes and free radicals. In addition to the complex nature of the immune response itself, the disease can also affect a number of targets. As well as the myelin sheath, other cells such as astrocytes and microglia can be attacked, forming discreet regions of damage known as plaques or lesions. The lesions are also known as scleroses (hence the name) and can occur in both the brain and the spinal cord. The sites of the lesions tend to be near blood vessels and are commonly found on the optic nerve, cerebellum, periventricular regions and spinal cord.

The initial mechanism for the onset of disease remains largely unknown and the number of active lesions at any given time is actually quite low. The heterogeneous nature of the disease and the number of clinical subtypes that this creates suggest that MS is probably a series of related conditions rather than one disease.

DP IV-inhibitors were investigated in the EAE mouse, an animal model for MS (A. Steinbrecher, D. Reinhold, L. Quigley, A. Gado, N. Tresser, L. Izikson, I Born, J. Faust, K. Neubert, R. Martin, S. Ansorge, and S. Brocke. Targeting dipeptidyl peptidase IV (CD26) suppresses autoimmune encephalomyelitis and up-regulates TGF-beta 1 secretion in vivo. J Immunol 166 (3):2041-2048, 2001; A. Steinbrecher, D. Reinhold, L. Quigley, A. Gado, N. Tresser, L. Izikson, I Born, J. Faust, K. Neubert, R. Martin, S. Ansorge, and S. Brocke. Dipeptidyl peptidase IV in inflammatory CNS disease. Adv Exp Med Biol 477:145-153, 2000.)

Inhibitors of dipeptidyl peptidase IV exert anxiolytic-like action when administered centrally (icv) in rats. Chronic treatment with the antidepressant Imipramine has recently been demonstrated to reduce the severity of acute MPB-induce EAE in female Lewis rats (Stephan, M., Straub R. H., Breivik T., Pabst, R. and Hörsten, S. v. Postnatal maternal deprivation aggravates experimental autoimmune encephalomyelitis (EAE) in adult Lewis rats: reversal by chronic imipramine treatment. Int. J. Dev. Neurosci. in press (2002)).

Several studies have underlined the importance of the relationship between stressful life events, psychological distress, and clinical exacerbation of multiple sclerosis (MS) in humans. Stress modulates the course of EAE in rats (Dimitrijevic, M., Laban, O., Hörsten, S. v., Markovic, B. M. & Jankovic, B. D. (1994). Neonatal sound stress and development of experimental allergic encephalomyelitis in Lewis and DA rats. Int J Neurosci, 78, 135-43; Laban, O., Dimitrijevic, M., Hörsten, S. v., Markovic, B. M. & Jankovic, B. D. (1995). Experimental allergic encephalomyelitis in adult DA rats subjected to neonatal handling or gentling. Brain Res, 676, 133-40.). Stress protection is currently not considered as a treatment option for MS.

Further examples of low molecular weight dipeptidyl peptidase IV inhibitors are agents such as tetrahydroisoquinolin-3-carboxamide derivatives, N-substituted 2-cyanopyroles and -pyrrolidines, N-(N'-substituted glycyl)-2-cyanopyrrolidines, N-(substituted glycyl)-thiazolidines, N-(substituted glycyl)-4-cyanothiazolidines, amino-acyl-borono-prolyl-inhibitors and cyclopropyl-fused pyrrolidines. Inhibitors of dipeptidyl peptidase IV are described in U.S. Pat. Nos. 6,011,155; 6,107,317; 6,110,949; 6,124,305; 6,172,081; WO 99/61431, WO 99/67278, WO 99/67279, DE 198 34 591, WO 97/40832, DE 196 16 486 C 2, WO 98/19998, WO 00/07617, WO 99/38501, WO 99/46272, WO 99/38501, WO 01/68603, WO 01/40180, WO 01/81337, WO 01/81304, WO 01/55105, WO 02/02560 and WO 02/14271, the teachings of which are herein incorporated by reference in their entirety.

SUMMARY OF THE INVENTION

The present invention provides a new use of DP IV-inhibitors. The compounds of formulas 1 to 12, and their corresponding pharmaceutically acceptable acid addition salt forms, are useful in treating conditions mediated by DP IV or DP IV-like enzymes, such as immune, autoimmune or central nervous system disorders selected from the group consisting of strokes, tumors, ischemia, Parkinson's disease, and migraines. In a more preferred embodiment, the compounds of the present invention are useful for the treatment of multiple sclerosis.

DETAILED DESCRIPTION OF THE INVENTION

Figure 1:
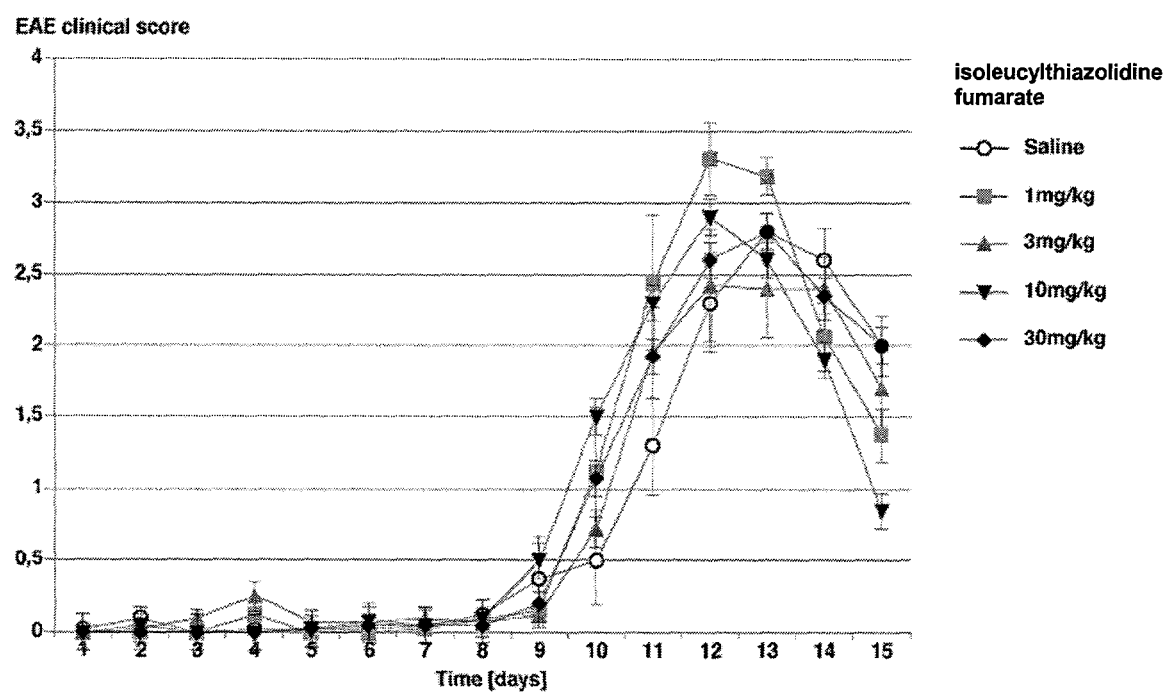
FIG. 1: Illustrates the clinical course of experimental autoimmune encephalomyelitis (EAE). The effects of different dosages of isoleucyl thiazolidine fumarate on the clinical course of EAE in adult female Lewis rats were studied. Symbols represent means±SEM of the mean clinical score per day. Two factor ANOVA for repeated measures revealed a significant a significant interaction between the factors "treatment"בclinical score over time" indicating that during the initial acute phase of the disease between day 9-12(13), the DPIV inhibitors aggravated the disease while during between day 13-15 inhibitor they improved or accelerated recovery from disease.
Figure 2:
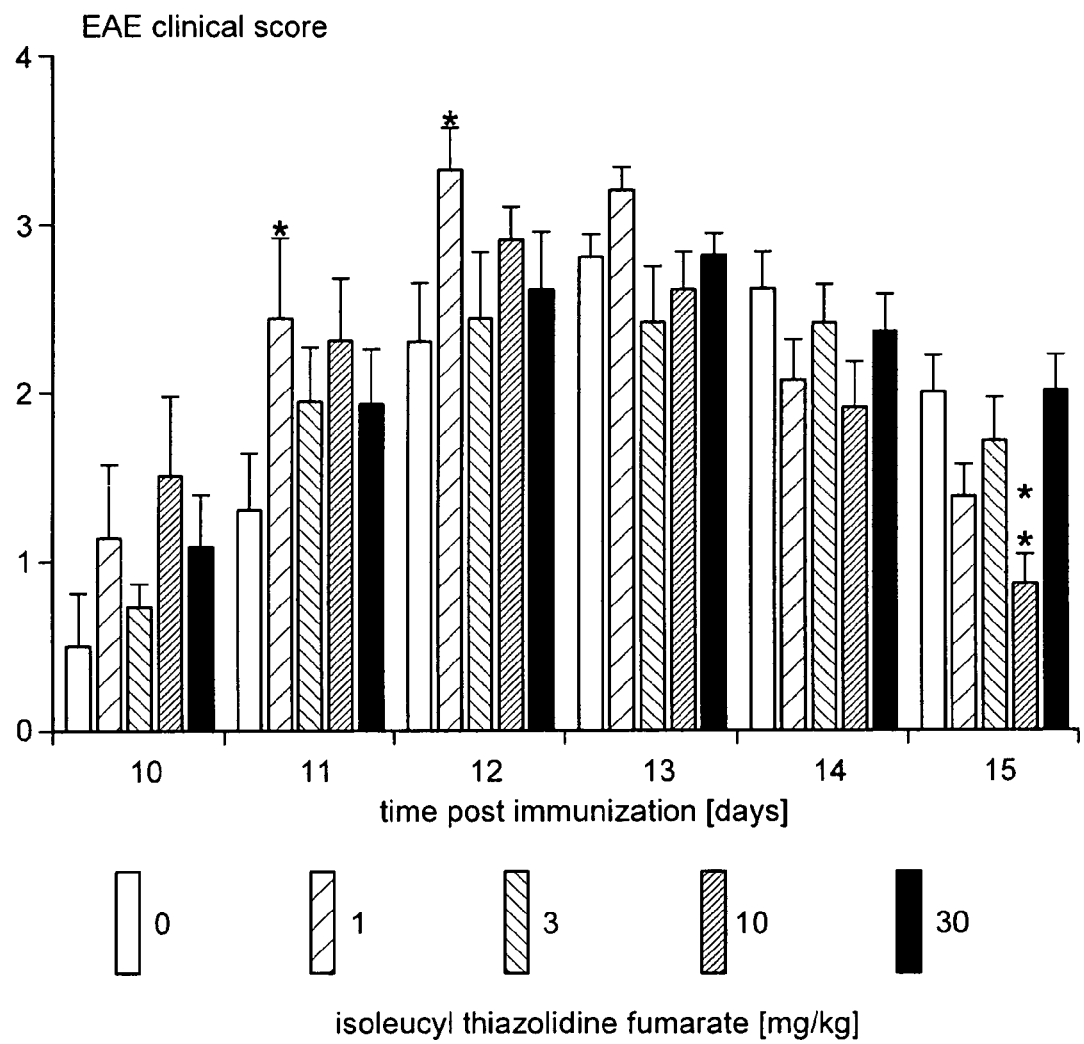
FIG. 2: Illustrates the clinical course of experimental autoimmune encephalomyelitis (EAE) in isoleucyl thiazolidine fumarate treated rats split by days 10-15 post immunization. Separate one factor ANOVAs revealed significant disease-aggravating effect at the 1 mg dosage on day 11 and 12 p.i., while the 10 mg dose significantly reduced clinical score at day 15 p.i. This indicates that the inhibitor initially tends to aggravate the disease while at later stages it results in an accelerated recovery from disease. Columns represent means±SEM of the mean clinical score per day. Asterisks indicate significant post-hoc effects in the PLSD test with *<0.05 and **<0.001.

The present invention relates to the area of dipeptidyl peptidase IV (DP IV) inhibition and, more particularly, to a new use of inhibitors of DP IV and DP IV-like enzyme activity for the treatment of neuronal and immune disorders, in particular for the treatment of multiple sclerosis, and pharmaceutical compositions containing said compounds.

In one illustrative embodiment, the present invention relates to dipeptide compounds and compounds analogous to dipeptide compounds that are formed from an amino acid and a thiazolidine or pyrrolidine group, and salts thereof, referred to hereinafter as dipeptide compounds.

The use of such compounds as inhibitors of DP IV or of DP IV-analogous enzyme activity is already known from DD 296 075, PCT/DE 97/00820 and PCT/EP 99/03712.

Especially suitable for that purpose according to the invention are dipeptide compounds in which the amino acid is selected from a natural amino acid, such as, for example, leucine, valine, glutamine, glutamic acid, proline, isoleucine, asparagines and aspartic acid.

The dipeptide compounds according to the invention exhibit at a concentration (of dipeptide compounds) of 10 µM, especially under the conditions indicated in Table 1, a reduction in the activity of dipeptidyl peptidase IV or DP IV-analogous enzyme activities of at least 10%, especially of at least 40%. Frequently a reduction in activity of at least 60% or at least 70% is also required. Preferred effectors may also exhibit a reduction in activity of a maximum of 20% or 30%.

Preferred compounds are L-allo-isoleucyl thiazolidine, L-threo-isoleucyl pyrrolidine and salts thereof, especially the fumaric salts, and L-allo-isoleucyl pyrrolidine and salts thereof. Especially preferred compounds are glutaminyl thiazolidine and glutaminyl pyrrolidine of formulas 1 and 2:

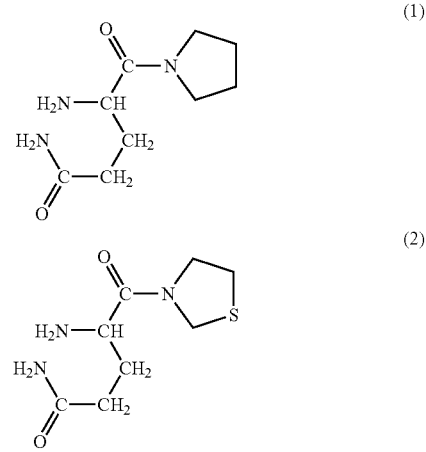

Further preferred compounds are given in Table 1.

The salts of the dipeptide compounds can be present in a molar ration of dipeptide (-analogous) component to salt component of 1:1 or 2:1. Such a salt is, for example, (Ile-Thia)$_2$ fumaric acid.

TABLE 1

Structures of further preferred dipeptide compounds

Effector

H-Asn-pyrrolidine
H-Asn-thiazolidine
H-Asn-pyrrolidine
H-Asn-thiazolidine
H-Asp(NHOH)-pyrrolidine
H-Asp(NHOH)-thiazolidine
H-Glu-pyrrolidine
H-Glu-thiazolidine
H-Glu(NHOH)-pyrrolidine

TABLE 1-continued

Structures of further preferred dipeptide compounds

| Effector |
|---|
| H-Glu(NHOH)-thiazolidine |
| H-His-pyrrolidine |
| H-His-thiazolidine |
| H-Pro-pyrrolidine |
| H-Pro-thiazolidine |
| H-Ile-azididine |
| H-Ile-pyrrolidine |
| H-L-allo-Ile-thiazolidine |
| H-Val-pyrrolidine |
| H-Val-thiazolidine |

In another preferred embodiment, the present invention provides peptide compounds of formula 3 useful for competitive modulation of dipeptidyl peptidase IV catalysis:

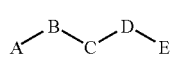

(3)

wherein
A, B, C, D and E are any amino acid residues including proteinogenic amino acids, non-proteinogenic amino acids, L-amino acids and D-amino acids and wherein E and/or D may be absent or B and/or A may be absent with additional conditions as hereinafter detailed:

Further conditions regarding formula (3):

A is any amino acid residue except D-amino acid residues;

B is any proteinogenic amino acid residue, but

If B is an amino acid selected from Pro, Ala, Ser, Gly, Hyp, acetidine-(2)-carboxylic acid or pipecolic acid, then C is any amino acid residue including D-amino acids, except Pro, Ala, Ser, Gly, Hyp, acetidine-(2)-carboxylic acid or pipecolic acid and E may be unused to generate tetrapeptides of the formula A-B-C-D, or D and E may be unused to generate tripeptides of the formula A-B-C provided, but If B is not an amino acid selected from Pro, Ala, Ser, Gly, Hyp, acetidine-(2)-carboxylic acid or pipecolic acid, then C is any α-amino acid except D-amino acids; D is Pro, Ala, Ser, Gly, Hyp, acetidine-(2)-carboxylic acid or pipecolic acid; E is any amino acid residue including D-amino acids, except Pro, Ala, Ser, Gly, Hyp, acetidine-(2)-carboxylic acid or pipecolic acid, but If D is Pro, Ala, Ser, Gly, Hyp, acetidine-(2)-carboxylic acid or pipecolic acid, then C is any α-amino acid except D-amino acids and Pro, Ala, Ser, Gly, Hyp, acetidine-(2)-carboxylic acid or pipecolic acid, and A may be unused to generate tetrapeptides of the formula B-C-D-E, or A and B may be unused to generate tripeptides of the formula C-D-E provided however, If D is not selected from Pro, Ala, Ser, Gly, Hyp, acetidine-(2)-carboxylic acid or pipecolic acid, then E is any amino acid residue including D-amino acids.

Proteinogenic amino acids are defined as natural protein-derived α-amino acids. Non-proteinogenic amino acids are defined as all other amino acids, which are not building blocks of common natural proteins.

The resulting peptides may be synthesized as the free C-terminal acid or as the C-terminal amide form. The free acid peptides or the amides may be varied by side chain modifications. Such side chain modifications are for instance, but not restricted to, homoserine formation, pyroglutamic acid formation, disulphide bond formation, deamidation of asparagine or glutamine residues, methylation, t-butylation, t-butyloxycarbonylation, 4-methylbenzylation, thioanysilation, thiocresylation, bencyloxymethylation, 4-nitrophenylation, bencyloxycarbonylation, 2-nitrobencoylation, 2-nitrosulphenylation, 4-toluenesulphonylation, pentafluorophenylation, diphenylmethylation, 2-chlorobenzyloxycarbonylation, 2,4,5-trichlorophenylation, 2-bromobenzyloxycarbonylation, 9-fluorenylmethyloxycarbonylation, triphenylmethylation, 2,2,5,7,8,-pentamethylchroman-6-sulphonylation, hydroxylation, oxidation of methionine, formylation, acetylation, anisylation, bencylation, bencoylation, trifluoroacetylation, carboxylation of aspartic acid or glutamic acid, phosphorylation, sulphation, cysteinylation, glycolysation with pentoses, deoxyhexoses, hexosamines, hexoses or N-acetylhexosamines, farnesylation, myristolysation, biotinylation, palmitoylation, stearoylation, geranylgeranylation, glutathionylation, 5'-adenosylation, ADP-ribosylation, modification with N-glycolylneuraminic acid, N-acetyineuraminic acid, pyridoxal phosphate, lipoic acid, 4'-phosphopantetheine, or N-hydroxysuccinimide.

In the compounds of formula (3), the amino acid residues comprising A, B, C, D, and E substituents are attached to the adjacent moiety according to standard nomenclature so that the amino-terminus (N-terminus) of the amino acids is drawn on the left and the carboxyl-terminus of the amino acid is drawn to the right.

Until the present invention by Applicants, known peptide substrates of the proline-specific serine protease dipeptidyl peptidase IV in vitro are the tripeptides Diprotin A (Ile-Pro-Ile), Diprotin B (Val-Pro-Leu) and Diprotin C (Val-Pro-Ile). Applicants have unexpectedly discovered that the compounds disclosed here act as substrates of dipeptidyl peptidase IV in vivo in a mammal and, in pharmacological doses, inhibit the physiological turnover of endogenous substrates by competitive catalysis.

Particularly preferred compounds of the present invention that could be useful as modulators of dipeptidyl peptidase IV and DP IV-like enzymes include those compounds which show $k_i$-values for DP IV binding, effectively in DP IV inhibition in vivo after i.v. and/or p.o. administration to Wistar rats Further preferred compounds according to the present invention are Peptidylketones of formula 4:

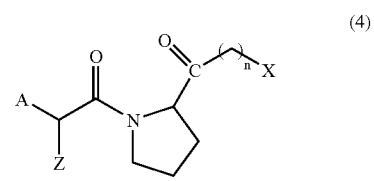

(4)

$n = 0, 1$ wherein
A is selected from:

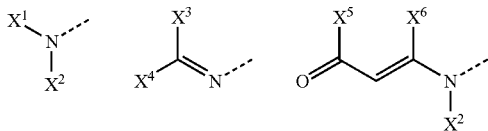

$X^1$ is H or a acyl or oxycarbonyl group incl. all amino acids and peptide residues, $X^2$ is H, —(CH)$_n$—NH—C$_5$H$_3$N—Y with n=2-4 or C$_5$H$_3$N—Y (a divalent pyridyl residue) and Y is selected from H, Br, Cl, I, NO$_2$ or CN, $X^3$ is H or selected from an alkyl, alkoxy, halogen, nitro, cyano or carboxy substituted phenyl or pyridyl residue, $X^4$ is H or selected from an alkyl, alkoxy, halogen, nitro, cyano or carboxy substituted phenyl or pyridyl residue, $X^5$ is H or an alkyl, alkoxy or phenyl residue, $X^6$ is H or a alkyl residue.

X for n=1
is selected from: H, OR$^2$, SR$^2$, NR$^2$R$^3$, N$^+$R$^2$R$^3$R$^4$, wherein:

R$^2$ stands for acyl residues, which are substituted with alkyl, cycloalkyl, aryl or heteroaryl residues, or for all amino acids and peptidic residues, or alkyl residues, which are substituted with alkyl, cycloalkyl, aryl and heteroaryl residues, R$^3$ stands for alkyl and acyl functions, wherein R$^2$ and R$^3$ may be embedded in ring structures of saturated and unsaturated carbocyclic or heterocyclic structures, R$^4$ stands for alkyl residues, wherein R$^2$ and R$^4$ or R$^3$ and R$^4$ may be embedded in ring structures of saturated and unsaturated carbocyclic or heterocyclic structures.

X for n=0
is selected from:

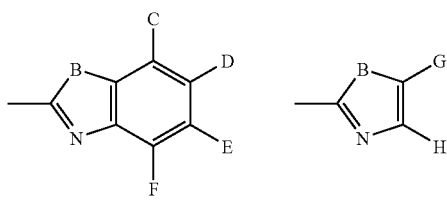

wherein
B stands for: O, S, NR$^5$, wherein R$^5$ is H, a alkyl or acyl,

C, D, E, F, G, H are independently selected from alkyl and substituted alkyl residues, oxyalkyl, thioalkyl, aminoalkyl, carbonylalkyl, acyl, carbamoyl, aryl and heteroaryl residues; and Z is selected from H, or a branched or single chain alkyl residue from C$_1$-C$_9$ or a branched or single chain alkenyl residue from C$_2$-C$_9$, a cycloalkyl residue from C$_3$-C$_8$, a cycloalkenyl residue from C$_5$-C$_7$, a aryl- or heteroaryl residue, or a side chain selected from all side chains of all natural amino acids or derivatives thereof.

Further, the present invention provides compounds of formulas 5, 6, 7,8, 9, 10 and 11, including all stereoisomers and pharmaceutical acceptable salts thereof,

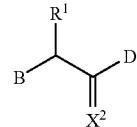

(5)

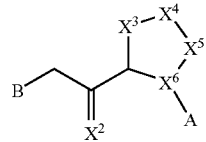

(6)

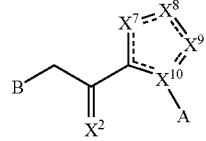

(7)

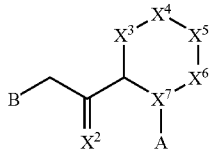

(8)

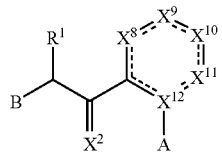

(9)

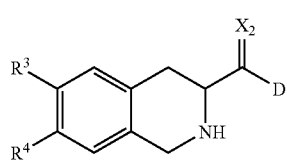

(10)

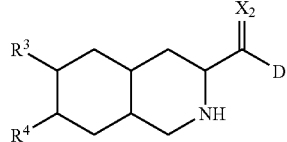

(11)

wherein:

R$^1$ is H, a branched or linear C$_1$-C$_9$ alkyl residue, a branched or linear C$_2$-C$_9$ alkenyl residue, a C$_3$-C$_8$ cycloalkyl-, C$_5$-C$_7$ cycloalkenyl-, aryl- or heteroaryl residue or a side chain of a natural amino acid or a derivative thereof, R$^3$ and R$^4$ are selected from H, hydroxy, alkyl, alkoxy, aryloxy, nitro, cyano or halogen, A is H or an isoster of an carbonic acid, like a functional group selected from CN, SO$_3$H, CONHOH, PO$_3$R$^5$R$^6$, tetrazole, amide, ester, anhydride, thiazole and imidazole, B is selected from:

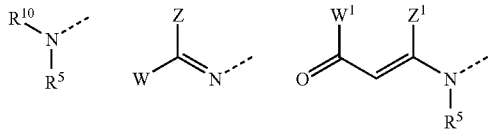

wherein:

R$^5$ is H, —(CH)$_n$—NH—C$_5$H$_3$N—Y with n=2-4 and C$_5$H$_3$N—Y (a divalent pyridyl residue) with Y=H, Br, Cl, I, NO$_2$ CN, R$^{10}$ is H, a acyl, oxycarbonyl or a amino acid residue, W is H or a phenyl or pyridyl residue, substituted with alkyl, alkoxy, halogen, nitro, cyano or carboxy residue, W$^1$ is H, a alkyl, alkoxy or phenyl residue, Z is H or a phenyl or pyridyl residue, substituted with alkyl, alkoxy, halogen, nitro, cyano or carboxy residue, Z$^1$ is H or a alkyl residue, D is a cyclic C$_4$-C$_7$ alkyl, C$_4$-C$_7$ alkenyl residue or a alkyl substituted derivative thereof or a cyclic 4-7-membered heteroalkyl or 4-7-membered heteroalkenyl residue, X$^2$ is O, NR$^6$, N$^+$(R$^7$)$_2$, or S, X$^3$ to X$^{12}$ are selected from CH$_2$, CR$^8$R$^9$, NR$^6$, N$^+$(R$^7$)$_2$, O, S, SO and SO$_2$, including all saturated and unsaturated structures, R$^6$, R$^7$, R$^8$, R$^9$ are selected from H, a branched or linear C$_1$-C$_9$ alkyl residue, a branched or lienar C$_2$-C$_9$ alkenyl residue, a C$_3$-C$_8$ cycloalkyl residue, a C$_5$-C$_7$ cycloalkenyl residue, an aryl or heteroaryl residue, with the following provisions:

Formula 6: X$^6$ is CH if A is not H,

Formula 7: X$^{10}$ is C if A is not H,

Formula 8: X$^7$ is CH if A is not H,

Formula 9: X$^{12}$ is C if A is not H.

Because of the wide distribution of the protein in the body and the wide variety of mechanisms involving DP IV, DP IV activity and DP IV-related proteins, systemic therapy (enteral or parenteral administration) with DP IV-inhibitors can result in a series of undesirable side-effects.

It has been possible to show that side chain-modified substrates of the enzyme dipeptidyl peptidase IV can be recognised by the enzyme and cleaved in the same way as unmodified substrates (DEMUTH, H.-U., HEINS, J., 1995).

For example, it has been possible to show that phosphorylated dipeptide-(B)-p-nitroanilides [KASPARI, A., et al., 1996] are substrates of DP IV. DP IV-inhibitors such as, for example, Glu(Gly)-Thia or Lys(Z-NO$_2$)-Thia [REINHOLD, D., et al., 1998] are transported completely.

The problem to be solved consisted in preparing compounds that can be used for targeted influencing of locally limited pathophysiological and physiological processes. The problem of the invention especially consists in obtaining locally limited inhibition of DP IV or DP IV-analogous activity for the purpose of targeted intervention in the regulation of the activity of locally active substrates.

This problem is solved according to the invention by providing compounds of the general formula (12)

 (12)

wherein

A is an amino acid having at least one functional group in the side chain,

B is a chemical compound covalently bound to at least one functional group of the side chain of A, namely
oligopeptides having a chain length of up to 20 amino acids, except for homopolymers of glycine consisting of up to 6 glycine monomers, or
polyethylene glycols having molar masses of up to 20 000 g/mol, and C is a thiazolidine, pyrrolidine, cyanopyrrolidine, hydroxyproline, dehydroproline or piperidine group amide-bonded to A.

In accordance with the invention, pharmaceutical compositions are provided comprising at least one compound of the general formula (12)

 (12)

wherein

A is an amino acid, preferably an α-amino acid, especially a natural α-amino acid having at least one functional group in the side chain, preferably threonine, tyrosine, serine, arginine, lysine, aspartic acid, glutamic acid or cysteine, B is a chemical compound covalently bound to at least one functional group in the side chain of A, namely oligopeptides having a chain length of up to 20 amino acids, polyethylene glycols having molar masses of up to 20 000 g/mol, optionally substituted organic amines, amides, alcohols, acids or aromatic compounds having from 8 to 50 C atoms, C is a thiazolidine, pyrrolidine, cyanopyrrolidine, hydroxyproline, dehydroproline or piperidine group amide-bonded to A, and at least one customary adjuvant appropriate for the site of action.

Throughout the description and the claims for the compounds of formula (12), the expression "alkyl" can denote a C$_{1-50}$ alkyl group, preferably a C$_{6-30}$ alkyl group, especially a C$_{8-12}$ alkyl group; for example, an alkyl group may be a methyl, ethyl, propyl, isopropyl or butyl group. The expression "alk", for example in the expression "alkoxy", and the expression "alkan", for example in the expression "alkanoyl", are defined as for "alkyl"; aromatic compounds are preferably substituted or optionally unsubstituted phenyl, benzyl, naphthyl, biphenyl or anthracene groups, which preferably have at least 8 C atoms; the expression "alkenyl" can denote a C$_{2-10}$ alkenyl group, preferably a C$_{2-6}$ alkenyl group, which has the double bond(s) at any desired location and may be substituted or unsubstituted; the expression "alkynyl" can denote a C$_{2-10}$ alkynyl group, preferably a C$_{2-6}$ alkynyl group, which has the triple bond(s) at any desired location and may be substituted or unsubstituted; the expression "substituted" or substituent can denote any desired substitution by one or more, preferably one or two, alkyl, alkenyl, alkynyl, mono- or multi-valent acyl, alkanoyl, alkoxyalkanoyl or alkoxyalkyl groups; the aforementioned substituents may in turn have one or more (but preferably zero) alkyl, alkenyl, alkynyl, mono- or multivalent acyl, alkanoyl, alkoxyalkanoyl or alkoxyalkyl groups as side groups; organic amines, amides, alcohols or acids, each having from 8 to 50 C atoms, preferably from 10 to 20 C atoms, can have the formulae (alkyl)$_2$N— or alkyl-NH—, —CO—N(alkyl)$_2$ or —CO—NH(alkyl), -alkyl-OH or -alkyl-COOH.

Despite an extended side chain function, the compounds of formula (12) can still bind to the active centre of the enzyme dipeptidyl peptidase IV and analogous enzymes but are no longer actively transported by the peptide transporter PepT1. The resulting reduced or greatly restricted transportability of the compounds according to the invention leads, in ideal manner, to local or site directed inhibition of DP IV and DP IV-like enzyme activity.

The compounds of formula (12) or compounds used in accordance with the invention can be present or used, respectively, in the form of racemates or in the form of enantiomerically pure compounds, preferably in the L-threo or L-allo form with respect to part A of formula (12).

By extending/expanding the side chain modifications, for example beyond a number of seven carbon atoms, it is accordingly possible to obtain a dramatic reduction in transportability (see Example 12). The Examples in Table 12.1 clearly show that, with increasing spatial size of the side chains, there is a reduction in the transportability of the substances. By spatially and sterically expanding the side chains, for example beyond the atom group size of a monosubstituted phenyl radical, hydroxylamine radical or amino acid residue, it is possible according to the invention to modify or suppress the transportability of the target substances.

According to the present invention, the compounds of formula (12) inhibit DP IV or DP IV-like enzyme activity in the body of a mammal in a site specific manner. It is accordingly possible to influence local physiological and pathophysiological conditions (inflammation, psoriasis, arthritis, autoimmune diseases, allergies) effectively and with dramatically reduced side-effects.

Preferred compounds of formula (12) are compounds, wherein the oligopeptides have chain lengths of from 3 to 15, especially from 4 to 10, amino acids, and/or the polyethylene glycols have molar masses of at least 250 g/mol, preferably of at least 1500 g/mol and up to 15 000 g/mol, and/or the optionally substituted organic amines, amides, alcohols, acids or aromatic compounds have at least 12 C atoms and preferably up to 30 C atoms.

The compounds of the present invention can be converted into acid addition salts, especially pharmaceutically acceptable acid addition salts. The pharmaceutically acceptable salt generally takes a form in which an amino acids basic side chain is protonated with an inorganic or organic acid. Representative organic or inorganic acids include hydrochloric, hydrobromic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toulenesulfonic, cyclohexanesulfamic, salicylic, saccharinic or trifluoroacetic acid. All pharmaceutically acceptable acid addition salt forms of the compounds of formulas I and II are intended to be embraced by the scope of this invention.

In view of the close relationship between the free compounds and the compounds in the form of their salts, whenever a compound is referred to in this context, a corresponding salt is also intended, provided such is possible or appropriate under the circumstances.

The present invention further includes within its scope prodrugs of the compounds of this invention. In general, such prodrugs will be functional derivatives of the compounds which are readily convertible in vivo into the desired therapeutically active compound. Thus, in these cases, the methods of treatment of the present invention, the term "administering" shall encompass the treatment of the various disorders described with prodrug versions of one or more of the claimed compounds, but which converts to the above specified compound in vivo after administration to the subject. Conventional procedures for the selection and preparation of suitable prodrug derivatives are described, for example, in "Design of Prodrugs", ed. H. Bundgaard, Elsevier, 1985 and the patent applications DE 198 28 113 and DE 198 28 114, which are fully incorporated herein by reference.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms of the compounds may exist as polymorphs and as such are intended to be included in the present invention. In addition, some of the compounds may form solvates with water (i.e. hydrates) or common organic solvents, and such solvates are also intended to be encompassed within the scope of this invention.

The compounds, including their salts, can also be obtained in the form of their hydrates, or include other solvents used for their crystallization.

As indicated above, the compounds of the present invention, and their corresponding pharmaceutically acceptable acid addition salt forms, are useful in inhibiting DP IV and DP IV-like enzyme activity. The ability of the compounds of the present invention, and their corresponding pharmaceutically acceptable acid addition salt forms to inhibit DP IV and DP IV-like enzyme activity may be demonstrated employing the DP IV activity assay for determination of the $K_i$-values and the $IC_{50}$-values in vitro, as described in examples 7 and 8.

The ability of the compounds of the present invention, and their corresponding pharmaceutically acceptable acid addition salt forms to inhibit DP IV may be demonstrated by oral or intravasal administration to Wistar rats, as described in example 11. The compounds of the present invention inhibit DP IV activity in vivo after both, oral and intravasal administration to Wistar rats.

DP IV is present in a wide variety of mammalian organs and tissues e.g. the intestinal brush-border (Gutschmidt S. et al., "In situ"—measurements of protein contents in the brush border region along rat jejunal villi and their correlations with four enzyme activities. Histochemistry 1981, 72 (3), 467-79), exocrine epithelia, hepatocytes, renal tubuli, endothelia, myofibroblasts (Feller A. C. et al., A monoclonal antibody detecting dipeptidylpeptidase IV in human tissue. Virchows Arch. A. Pathol. Anat. Histopathol. 1986; 409 (2):263-73), nerve cells, lateral membranes of certain surface epithelia, e.g. Fallopian tube, uterus and vesicular gland, in the luminal cytoplasm of e.g., vesicular gland epithelium, and in mucous cells of Brunner's gland (Hartel S. et al., Dipeptidyl peptidase (DPP) IV in rat organs. Comparison of immunohistochemistry and activity histochemistry. Histochemistry 1988; 89 (2): 151-61), reproductive organs, e.g. cauda epididymis and ampulla, seminal vesicles and their secretions (Agrawal & Vanha-Perttula, Dipeptidyl peptidases in bovine reproductive organs and secretions. Int. J. Androl. 1986, 9 (6): 435-52). In human serum, two molecular forms of dipeptidyl peptidase are present (Krepela E. et al., Demonstration of two molecular forms of dipeptidyl peptidase IV in normal human serum. Physiol. Bohemoslov. 1983, 32 (6): 486-96). The serum high molecular weight form of DP IV is expressed on the surface of activated T cells (Duke-Cohan J. S. et al., Serum high molecular weight dipeptidyl peptidase IV (CD26) is similar to a novel antigen DPPT-L released from activated T cells. J. Immunol. 1996, 156 (5): 1714-21).

The compounds of the present invention, and their corresponding pharmaceutically acceptable acid addition salt forms are able to inhibit DP IV in vivo. In one embodiment of the present invention, all molecular forms, homologues and epitopes of DP IV from all mammalian tissues and organs, also of those, which are undiscovered yet, are intended to be embraced by the scope of this invention.

Among the rare group of proline-specific proteases, DP IV was originally believed to be the only membrane-bound enzyme specific for proline as the penultimate residue at the amino-terminus of the polypeptide chain. However, other molecules, even structurally non-homologous with the DP IV but bearing corresponding enzyme activity, have been identified recently. DP IV-like enzymes, which are identified so far, are e.g. fibroblast activation protein α, dipeptidyl peptidase IV β, dipeptidyl aminopeptidase-like protein, N-acetylated α-linked acidic dipeptidase, quiescent cell proline dipeptidase, dipeptidyl peptidase II, attractin and dipeptidyl peptidase IV related protein (DPP 8), and are described in the review article by Sedo & Malik (Sedo & Malik, Dipeptidyl peptidase IV-like molecules: homologous proteins or homologous activities? Biochimica et Biophysica Acta 2001, 36506: 1-10). In another preferred embodiment of the present invention, all molecular forms, homologues and epitopes of proteins comprising DP IV-like enzyme activity, from all mammalian tissues and organs, also of those, which are undiscovered yet, are intended to be embraced by the scope of this invention.

The ability of the compounds of the present invention, and their corresponding pharmaceutically acceptable acid addition salt forms to inhibit DP IV-like enzymes may be demonstrated employing an enzyme activity assay for determination of the $K_i$-values in vitro as described in example 9. The $K_i$-values of the compounds of the present invention against porcine dipeptidyl peptidase II were exemplary determined as $K_i=8.52*10^{-5}$ M±6.33*$10^{-6}$ M for glutaminylpyrrolidine and $K_i=1.07*10^{-5}$ M±3.81*$10^{-7}$ M for glutaminylthazolidine.

In another embodiment, the compounds of the present invention, and their corresponding pharmaceutically acceptable acid addition salt forms have only low, if no inhibitory activity against non-DP IV and non-DP IV- like proline specific enzymes. As described in example 10, with glutaminylthiazolidine and glutaminylpyrrolidine exemplarily, no inhibition of dipeptidyl peptidase I and prolyl oligopeptidase was found. Against prolidase, both compounds explained a marked lower efficacy compared to DP IV. The IC 50-values against prolidase were determined as IC 50>3 mM for glutaminylthiazolidine and as IC 50=3.4*$10^{-4}$M±5.63*$10^{-5}$ for glutaminylpyrrolidine.

In view of their ability to inhibit DP IV and DP IV-like enzyme activity, the compounds of the present invention, and their corresponding pharmaceutically acceptable acid addition salt forms, are useful in treating conditions mediated by said enzyme activities. Based on the findings described in the examples of the present invention and in the literature, it is expected, that the compounds disclosed herein are useful in the treatment of conditions such as non-insulin-dependent diabetes mellitus, arthritis, obesity, immune and autoimmune disorders, allograft transplantation, cancer, neuronal disorders and dermal diseases.

In a more preferred embodiment, the compounds of this invention, and their corresponding pharmaceutically acceptable acid addition salt forms, are useful for the treatment of multiple sclerosis. The ability of the compounds of the present invention, and their corresponding pharmaceutically acceptable acid addition salt forms, to alleviate the signs of multiple sclerosis can be determined employing the EAE model. The method is described in example 13.

The present invention therefore provides a method of treating a condition mediated by modulation of the DP IV or DP IV-like enzyme activity in a subject in need thereof which comprises administering any of the compounds of the present invention or pharmaceutical compositions thereof in a quantity and dosing regimen therapeutically effective to treat the condition. Additionally, the present invention includes the use of the compounds of this invention, and their corresponding pharmaceutically acceptable acid addition salt forms, for the preparation of a medicament for the treatment of a condition mediated by modulation of the DP IV activity in a subject. The compound may be administered to a patient by any conventional route of administration, including, but not limited to, intravenous, oral, subcutaneous, intramuscular, intradermal and parenteral.

In an further illustrative embodiment, the present invention provides formulations for the compounds of formulas 1 to 12, and their corresponding pharmaceutically acceptable acid addition salt forms, in pharmaceutical compositions.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human, being sought by a researcher, veterinarian, medical doctor or other clinician, which includes alleviation of the symptoms of the disease or disorder being treated.

As used herein, the term "composition" is intended to encompass a product comprising the claimed compounds in the therapeutically effective amounts, as well as any product which results, directly or indirectly, from combinations of the claimed compounds.

To prepare the pharmaceutical compositions of this invention, one or more compounds of formulas 1 to 12, and their corresponding pharmaceutically acceptable acid addition salt forms, as the active ingredient, is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives may advantageously include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are employed. If desired, tablets may be sugar coated or enteric coated by standard techniques. For parenterals the carrier will usually comprise sterile water, through other ingredients, for example, for purposes such as aiding solubility or for preservation, may be included.

Injectable suspensions may also prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit a dosage unit, e.g., tablet, capsule, powder, injection, suppository, teaspoonful and the like, of from about 0.03 mg to 100 mg/kg (preferably 0.1-30 mg/kg) and may be given at a dosage of from about 0.1-300 mg/kg/day (preferably 1-50 mg/kg/day). The dosages, however, may be varied depending upon the requirement of the patients, the severity of the condition being treated and the compound being employed. The use of either daily administration or post-periodic dosing may be employed. Typically the dosage will be regulated by the physician based on the characteristics of the patient, his/her condition and the therapeutic effect desired.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is ideally mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is ideally dispersed evenly throughout the composition so that the composition may be readily subdivided into equally effective dosage forms such as tablets, pills and capsules. This solid preformulation composition may then be subdivided into unit dosage forms of the type described above containing from 0.1 to about 500 mg of the active ingredient of the present invention.

The tablets or pills of the novel composition can be advantageously coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids with such materials as shellac, cetyl alcohol and cellulose acetate.

This liquid forms in which the novel compositions of the present invention may be advantageously incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991, fully incorporated herein by reference. The protecting groups may be removed at a convenient subsequent stage using methods known from the art.

The method of treating conditions modulated by dipeptidyl peptidase IV and DP IV-like enzymes described in the present invention may also be carried out using a pharmaceutical composition comprising any of the compounds as defined herein and a pharmaceutically acceptable carrier. The pharmaceutical composition may contain between about 0.01 mg and 1000 mg, preferably about 5 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds of the present invention can be administered in intranasal form via topical use of suitable intranasal vehicles, or via transdermal skin patches well known to those of ordinary skill in that art. To be administered in the form of transdermal delivery system, the dosage administration will, of course, be continuous rather than intermittent throughout the dosage regimen and dosage strength will need to be accordingly modified to obtain the desired therapeutic effects.

More preferably, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and other compounds known within the art.

The liquid forms in suitable flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines using processes well described in the art.

Compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyl eneoxidepolyllysine substituted with palmitoyl residue. Furthermore, compounds of the present invention may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of the addressed disorders is required.

The daily dosage of the products may be varied over a wide range from 0.01 to 1.000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.1 mg/kg to about 300 mg/kg of body weight per day. Preferably, the range is from about 1 to about 50 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, bioavailability due to the mode of administration, and the advancement of disease condition. In addition, factors associated with the particular patient being treated, including patient age, weight, diet and time of administration, should generally be considered in adjusting dosages.

To prepare the pharmaceutical compositions of this invention, one or more compounds of formulas I and II, and their corresponding pharmaceutically acceptable acid addition salt forms as the active ingredient, is ideally intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques.

For parenterals, the carrier will usually comprise sterile water, through other ingredients, for example, for purposes such as aiding solubility or for preservation, may be included. Injectable suspensions may also prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.03 mg to 100 mg/kg (preferred 0.1-30 mg/kg) and may be given at a dosage of from about 0.1-300 mg/kg/day (preferred 1-50 mg/kg/day). The dosages, however, may be varied depending upon the requirement of the patients, the severity of the condition being treated and the compound being employed. The use of either daily administration or post-periodic dosing may be employed.

EXAMPLES

Example 1

Synthesis of Dipeptide Compounds 1.1 General Synthesis of Ile-Thia*Salt

The Boc-protected amino acid BOC-Ile-OH is placed in ethyl acetate and the batch is cooled to about −5° C. N-Methylmorpholine is added dropwise, pivalic acid chloride (on a laboratory scale) or neohexanoyl chloride (on a pilot-plant scale) is added dropwise at constant temperature. The reaction is stirred for a few minutes for activation. N-Methylmorpholine (laboratory scale) and thiazolidine hydrochliride (laboratory scale) are added dropwise in succession, thiazolidine (pilot-plant scale) is added. Workingup in the laboratory is effected in conventional manner using salt solutions, on a pilot-plant scale the batch is purified with NaOH and $CH_3COOH$ solutions.

The removal of the BOC protecting group is carried out using HCl/dioxane (laboratory scale) or $H_2SO_4$ (pilot-plant scale). In the laboratory the hydrochloride is crystallised from EtOH/ether.

On a pilot-plant scale the free amine is prepared by the addition of $NaOH/NH_3$. Fumaric acid is dissolved in hot ethanol, the free amine is added dropwise, and (Ile-Thia)$^2$ furmarate (M=520.71 gmol$^{-1}$) precipitates. The analysis of isomers and enantiomers is carried out by electrophoresis.

1.2 Synthesis of Glutaminylpyrrolidine Free Base

Acylation:

N-Benzyl-oxycarbonylglutamine (2.02 g, 7.21 mmol) was dissolved in 35 ml THF and brought to −15° C. Into that mixture CAIBE (isobutylchloroformiate) (0.937 ml, 7.21 mmol) and 4-methylmorpholine (0.795 ml, 7.21 mmol) where added and the solution was stirred for 15 min. The formation of the mixed anhydride was checked by TLC (eluent: $CHCl_3$/MeOH:9/1). After warming to −10° C. pyrrolidine (0.596 ml, 7.21 mmol) was added. The mixture was brought to room temperature and stirred overnight.

Workup:

The sediment formed was filtered off and the solvent was evaporated. The resulting oil was taken up in ethylacetate (20 ml) and washed with a saturated solution of sodiumhydrogensulfate followed by a saturated solution of sodiumbicarbonate, water and brine. The organic layer was separated, dried and evaporated. The resulting product was checked for purity by TLC (eluent: $CHCl_3$/MeOH:9/1)

Yield: 1.18 g, waxy solid

Cleavage:

1.18 g of the resulting solid Z-protected compound was dissolved in 40 ml absolute ethanol. Into the solution ca. 20 mg Pd on charcoal (10%, FLUKA) was added and the suspension was shaken under a hydrogen atmosphere for 3 h. The progress of the reaction was monitored by TLC (eluent: $CHCl_3$/MeOH:9/1). After completion of the reaction the was removed to provide the free base.

Yield: 99%

The purity was checked by means of TLC: n-butanole/AcOH/water/ethylacetate: 1/1/1/1/, $R_f$=0.4. The identity of the reaction product was checked by NMR analysis.

1.3 Synthesis of Glutaminylthiazolidinehydrochloride

Acylation:

N-t-Butyl-oxycarbonylglutamine (2.0 g, 8.12 mmol) was dissolved in 5 ml THF and brought to −15° C. Into that mixture CAIBE (isobutylchloroformiate) (1.06 ml, 8.12 mmol) and 4-methylmorpholine (0.895 ml, 8.12 mmol) where added and the solution was stirred for 15 min. The formation of the mixed anhydride was checked by TLC (eluent: $CHCl_3$/MeOH:9/1). After warming to −10° C. another equivalent 4-methylmorpholine (0.895 ml, 8.12 mmol) and thiazolidinehydrochloride (1.02 g, 8.12 mmol was added. The mixture was brought to room temperature and stirred overnight.

Workup:

The sediment formed was filtered off and the solvent was evaporated. The resulting oil was taken up in chloroform (20 ml) and washed with a saturated solution of sodiumhydrogensulfate followed by a saturated solution of sodiumbicarbonate, water and brine. The organic layer was separated, dried and evaporated. The resulting product was checked for purity by TLC (eluent: $CHCl_3$/MeOH:9/1)

Yield: 1.64 g, solid

Cleavage:

640 mg of the resulting solid Boc-protected compound was dissolved in 3.1 ml ice cold HCl in dioxane (12.98 M, 20 equivalents) and left on ice. The progress of the reaction was monitored by TLC (eluent: $CHCl_3$/MeOH:9/1). After completion of the reaction the solvent was removed and the resulting oil was taken up in methanole and evaporated again. After that the resulting oil was dried over phosphorous-V-oxide and triturated two times with diethylether. The purity was checked by HPLC.

Yield: 0.265 g

The purity was checked by HPLC. The identity of the reaction product was checked by NMR analysis.

1.4 Synthesis of Glutaminylpyrrolidinehydrochloride

Acylation:

N-t-Butyl-oxycarbonylglutamine (3.0 g, 12.18 mmol) was dissolved in 7 ml THF and brought to −15° C. Into that mixture CAIBE (isobutylchloroformiate) (1.6 ml, 12.18 mmol) and 4-methylmorpholine (1.3 ml, 12.18 mmol) where added and the solution was stirred for 15 min. The formation of the mixed anhydride was checked by TLC (eluent: $CHCl_3$/MeOH:9/1). After warming to −10° C. 1 equivalent of pyrrolidine (1.0 ml, 12.18 mmol) was added. The mixture was brought to room temperature and stirred overnight.

Workup:

The sediment formed was filtered off and the solvent was evaporated. The resulting oil was taken up in chloroform (20 ml) and washed with a saturated solution of sodiumhydrogensulfate followed by a saturated solution of sodiumbicarbonate, water and brine. The organic layer was separated, dried and evaporated. The resulting product was checked for purity by TLC (eluent: $CHCl_3$/MeOH:9/1)

Yield: 2.7 g solid

Cleavage:

2.7 g of the resulting solid was dissolved in 13.0 ml ice cold HCl in dioxane (12.98 M, 20 equivalents) and left on ice. The progress of the reaction was monitored by TLC (eluent: $CHCl_3$/MeOH:9/1). After completion of the reaction the solvent was removed and the resulting oil was taken up in methanole and evaporated again. After that the resulting oil was dried over phosphorous-V-oxide and triturated two times with diethylether.

Yield: 980 mg

The purity was checked by HPLC. The identity of the reaction product was checked by NMR analysis.

Example 2

Chemical Characterization of Selected Dipeptide Compounds 2.1 Melting Point Determination Melting points were determined on a Kofler heating platform microscope from Leica Aktiengesellschaft, the values are not corrected, or on a DSC apparatus (Heumann-Pharma).

2.2 Optical Rotation

The rotation values were recorded at different wavelengths on a "Polarimeter 341" or higher, from the Perkin-Elmer company.

2.3 Measurement Conditions for the Mass Spectroscopy

The mass spectra were recorded by means of electrospray ionisation (ESI) on an "API 165" or API 365" from the PE Sciex company. The operation is carried out using an approximate concentration of c=10 μg/ml, the substance is taken up in MeOH/H₂O 50:50, 0.1% HCO₂H, the infusion is effected using a spray pump (20 μl/min). The measurement were made in positive mode [M+H]⁺, the ESI voltage is U=5600V.

2.4. Results 2.4.1 Tests on Ile-Thia*Fumarate (Isomer)

| Substance | Mp (° C.) | CE (min) | MS | [α]H₂O |
|---|---|---|---|---|
| L-threo-IT*F | 150$^{DSC}$ | 160 | 203 | −10.7 (405 nm) |
| D-threo-IT*F | 147 | 158 | 203 | not determined |
| L-allo-IT*F | 145-6 | 154 | 203 | −4.58 (380 nm) |
| D-allo-IT*F | 144-6 | 150 | 203 | 4.5 (380 nm) |

IT*F = isoleucyl thiazolidine fumarate
The NMR and HPLC data confirm the identity of the substance in question.
$^{DSC}$ = Differential Scanning Calorimetry 2.4.2 Tests on other Ile-Thia Salts

| IT*salt | M (gmol⁻¹) | MP (° C.) |
|---|---|---|
| succinate | 522.73 | 116 |
| tartrate | 352.41 | 122 |
| fumarate | 520.71 | 156 |
| hydrochloride | 238.77 | 169 |
| phosphate | 300.32 | 105 |

Example 3

Synthesis of Xaa-Pro-Yaa Tripeptides

All syntheses were carried out on a peptide synthesizer SP 650 (Labortec AG) applying Fmoc/tBu-strategy. Protected amino acids were purchased from Novabiochem or Bachem. trifluoro acetic acid (TFA) was purchased from Merck, triisopropyl silane (TIS) was purchased from Fluka.

Pre-loaded Fmoc-Yaa-Wang resin (2.8 g/substitution level 0.57 mmol/g) was deprotected using 20% piperidine/ N,N-dimethylformamide (DMF). After washing with DMF a solution of 2 eq (1.1 g) of Fmoc-Pro-OH were solved in DMF (12 ml solvent per gram resin). 2eq (1.04 g) of 2-(1H-Benzotriazole 1-yl)-1,1,3,3-tetramethyluronium tetrafluoroborate (TBTU) and 4 eq (1.11 ml) of N,N-diisopropylethylamine (DIEA) were added and placed in the reaction vessel. The mixture was shaken at room temperature for 20 minutes. Then the coupling cycle was repeated. After subsequent washing with DMF, dichlormethane, isopropanol and diethyl ether the resulting Fmoc-Pro-Ile-Wang resin was dried and then divided into 6 parts before coupling the last amino acid derivative.

Fmoc protecting group was removed as described above. After that 0.54 mmol of the Boc-amino acid, 0.54 mmol TBTU and 0.108 mmol DIEA in DMF were shaken for 20 min. The coupling cycle was repeated. Finally the peptide resin was washed and dried described above.

The peptide was cleaved from the resin using a mixture of trifluoroacetic acid (TFA) for 2.5 h, containing the following scavengers: TFA/H2O/triisipropylsilane (TIS)=9.5/0.25/ 0.25

The yields of crude peptides were 80-90% on the average. The crude peptide was purified by HPLC on a Nucleosil C18 column (7 μm, 250*21.20 mm, 100 A) using a linear gradient of 0.1% TFA/H2O with increasing concentration of 0.1% TFA/acetonitrile (from 5% to 65% in 40 min) at 6 ml/min.

The pure peptide was obtained by lyophilization, identified by Electrospray mass spectrometry and HPLC analysis.

3.1 Results—Identification of Xaa-Pro-Yaa Tripeptides After Chemical Synthesis

| Peptide | Mass (calc.) | Mass (exp.)[1] [M + H⁺] | HPLC k'[2] |
|---|---|---|---|
| Abu-Pro-Ile | 313.4 | 314.0 | 5.7 |
| Cha-Pro-Ile | 381.52 | 382.0 | 10.4 |
| Nva-Pro-Ile | 327.43 | 328.2 | 6.82 |
| Phg-Pro-Ile | 361.44 | 362.2 | 7.9 |
| Nle-Pro-Ile | 341.45 | 342.2 | 8.09 |
| Pip-Pro-Ile | 338.56 | 340.0 | 6.5 |
| Thr-Pro-Ile | 329.4 | 330.0 | 5.12 |
| Trp-Pro-Ile | 414.51 | 415.2 | 9.85 |
| Phe-Pro-Ile | 375.47 | 376.2 | 8.96 |
| Ser-Pro-Ile | 315.37 | 316.3 | 5.24 |
| Ser(P)-Pro-Ile | 395.37 | 396.0 | 3.35 |
| Tyr(P)-Pro-Ile | 471.47 | 472.3 | 5.14 |
| Val-Pro-Val | 313.4 | 314.0 | 5.07 |
| Ile-Pro-Val | 327.43 | 328.5 | 6.41 |
| Ile-Pro-allo-Ile | 341.4 | 342.0 | 7.72 |
| Val-Pro-allo-Ile | 327.4 | 328.5 | 6.51 |
| Tyr-Pro-allo-Ile | 391.5 | 392.0 | 7.02 |
| 2-Amino octanoic acid-Pro-Ile | 369.5 | 370.2 | 10.63 |
| Ser(Bzl)-Pro-Ile | 405.49 | 406.0 | 9.87 |
| Orn-Pro-Ile | 342.42 | 343.1 | 3.73 |
| Tic-Pro-Ile | 387.46 | 388.0 | 8.57 |
| Aze-Pro-Ile | 311.4 | 312.4 | 5.29 |
| Aib-Pro-Ile | 313.4 | 314.0 | 5.25 |
| t-butyl-Gly-Pro-Ile | 341.47 | 342.1 | 7.16 |
| Ile-Hyp-Ile | 356.45 | 358.2 | 6.57 |
| t-butyl-Gly-Pro-Val | 327.4 | 328.4 | 6.32 |
| -t--butyl-Gly-Pro-Gly | 285.4 | 286.3 | 3.74 |
| t-butyl-Gly-Pro-Ile-amide | 340.47 | 341.3 | 7.8 |
| t-butyl Gly-Pro-D-Val | 327.4 | 328.6 | 7.27 |
| t-butyl-Gly-Pro-t-butyl-Gly | 341.24 | 342.5 | 9.09 |
| Ile-Pro-t-butyl-Gly | 341.47 | 342.36 | 6.93 |
| Val-Pro-t-butyl-Gly | 327.4 | 328.15 | 5.98 |

[1][M + H⁺] were determined by Electrospray mass spectrometry in positive ionization mode.
[2]RP-HPLC conditions:
column: LiChrospher 100 RP 18 (5 μm), 125 × 4 mm
detection (UV): 214 nm
gradient system: acetonitrile (ACN)/H₂O (0.1% TFA) from 5% ACN to 50% in 15 min,
flow: 1 ml/min
$k' = (t_r - t_0)/t_0$
$t_0$ = 1.16 min
t-butyl-Gly is defined as:

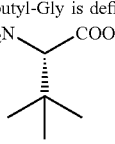

Example 4
Synthesis of Peptidylketones
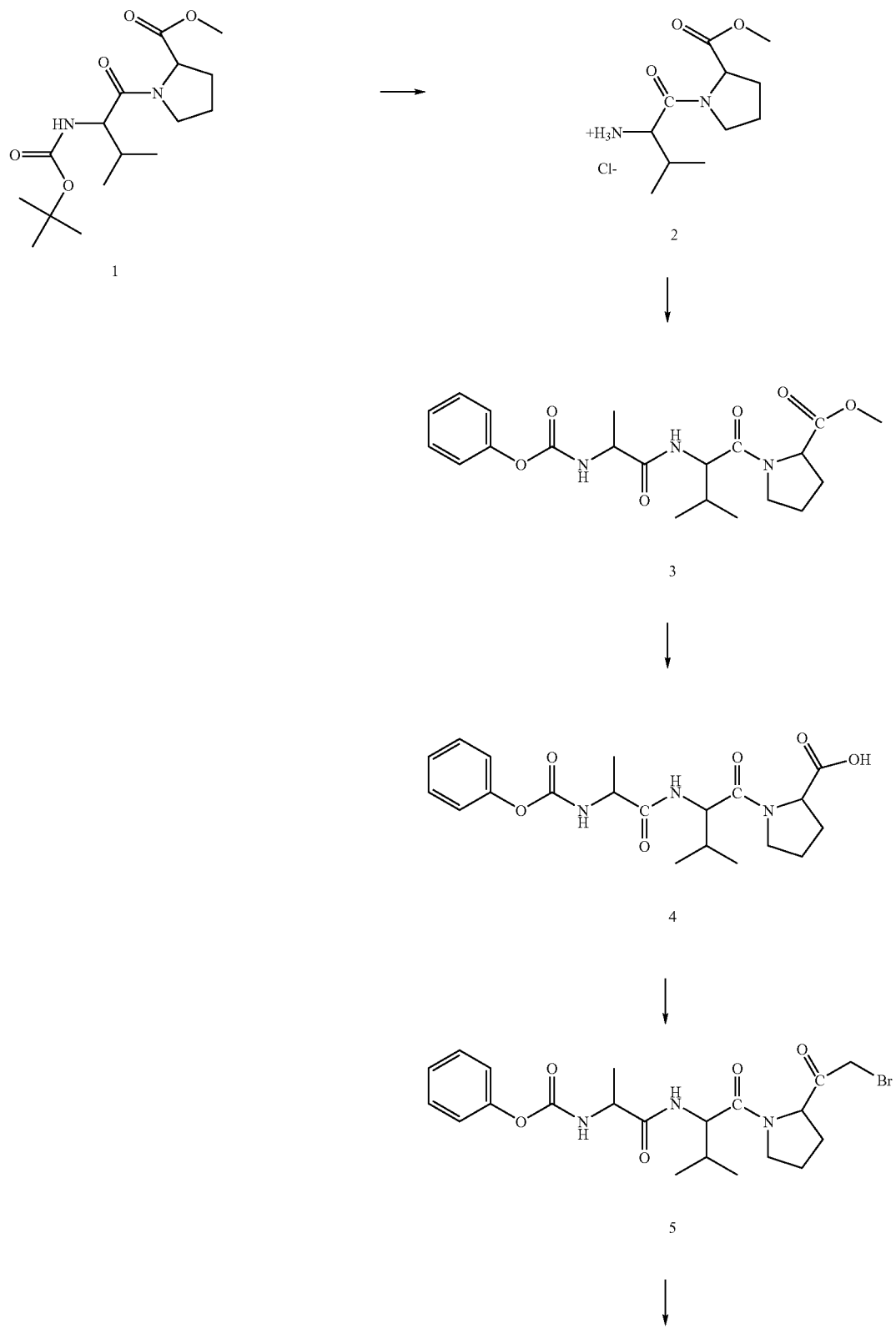

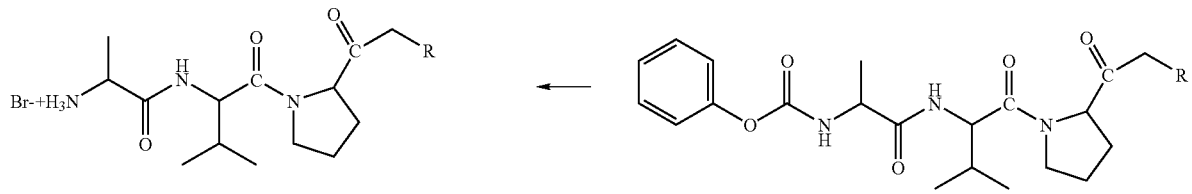

8: R = OC(O)Ac
9: R = OC(O)Ph

6: R = OC(O)Ac
7: R = OC(O)Ph

H-Val-Pro-OMe*HCl 2

Boc-Val-OH (3.00 g, 13.8 mmol) was dissolved in 10 ml of dry THF and cooled down to −15° C. To the mixture CAIBE (1.80 ml, 13.8 mmol) and NMM (1.52 ml, 13.8 mmol) where added and the solution was stirred until the formation of the mixed anhydride was complete. Then the mixture was brought to −10° C. and NMM (1.52 ml, 13.8 mmol) was added followed by H-Pro-OMe*HCl (2.29 g, 13.8 mmol). The mixture was allowed to reach room temperature and left overnight. After removing the solvent and the usual workup the resulting ester 1 was taken without further characterisation. The ester 1 was dissolved in HCl/HOAc (5 ml, 6N) and left at 0° C. until the removal of the Boc-group was complete. The solvent was then removed and the resulting oil was treated with diethylether to give a white solid 2.

Yield: 2.5 g, 80%

Z-Ala-Val-Pro-OMe 3

Z-Ala OH (3.5 g, 15.7 mmol) and 2 (4.18 g, 15.7 mmol) where treated in the same manner as above for 1, to give 3 as a white solid.

Yield: 4.2 g, 64%

Z-Ala-Val-Pro-OH 4

3 (4.2 g, 9.6 mmol) was dissolved in 30 ml of water/acetone (1/5 v/v) and 11.6 ml NaOH (1N) where added. After completion of the reaction the organic solvent was removed by evaporation and the resulting solution was diluted by 15 ml NaHCO$_3$ solution (saturated). Then the mixture was extracted three times by 10 ml of acetic acid ethyl ester. After that the solution was brought to pH2 by adding HCl (15% in water). The resulting mixture was extracted three times by 30 ml of acetic acid ethyl ester. The organic layer was separated and washed three times with brine, dried (Na$_2$SO$_4$) and evaporated.

Yield: 3.5 g, 87%

Z-Ala-Val-Pro-CH$_2$—Br 5

4 (2.00 g, 4.76 mmol) was dissolved in 15 ml of dry THF and converted into a mixed anhydride (see compound 1) using CAIBE (0.623 ml, 4.76 mmol) and NMM (0.525 ml, 4.76 mmol). The precipitate formed was filtered off and cooled down to −15° C. Then diazomethane (23.8 mmol in 30 ml ether) was dropped into the solution under an argon atmosphere. After leaving the mixture for 1 h at 0° C. 1.27 ml of HBr (33% in AcOH) was added and the solution was stirred for 30 min at room temperature . . . . After that 70 ml of ether was added and the mixture was washed with 20 ml of water. The organic layer was separated and dried (Na$_2$SO$_4$) and evaporated.

Yield (crude): 1.8 g, 80%

Z-Protected Acyloxymethylene Ketones

The acid (2eq) was dissolved in DMF and an equimolar amount of KF was added. The suspension was allowed to stir at room temperature for 1 hour. Then the brommethylene (1eq) component was added and the solution was allowed to stir overnight. After that the solvent was removed under vacuum and the resulting oil was dissolved in chloroform and washed with brine. Then the organic layer was separated dried (Na$_2$SO$_4$) and the solvent was removed. The product was purified by column chromatography using silica gel and heptane/chloroform.

Z-Ala-Val-Pro-CH$_2$O—C(O)—CH$_3$ 6

Acetic acid (230 μl, 4.02 mmol), KF (0.234 g, 4.02 mmol), 5 (1.00 g, 2.01 mmol)

Yield: 0.351 g, 36%

Z-Ala-Val-Pro-CH$_2$O—C(O)-Ph 7

Benzoic acid (0.275 g, 2.25 mmol), KF (0.131 mg, 2.25 mmol), 5 (0.56 g. 1.13 mmol)

Yield: 0.34 g, 56%

Deprotection

The Z-protected compound was dissolved in HBr/AcOH and stirred. When the reaction was complete ether was added, the white precipitate formed was filtered off and dried.

H-Ala-Val-Pro-CH$_2$O—C(O)CH$_3$*HBr 8

6 (0.351 g, 0,73 mmol)

Yield: 0.252 g, 98%

H-Ala-Val-Pro-CH$_2$O—C(O)Ph*HBr 9

7 (0.34 g, 0.63 mmol)

Yield: 0,251 g, 99%

Example 5

Synthesis Of Cycloalkylketones

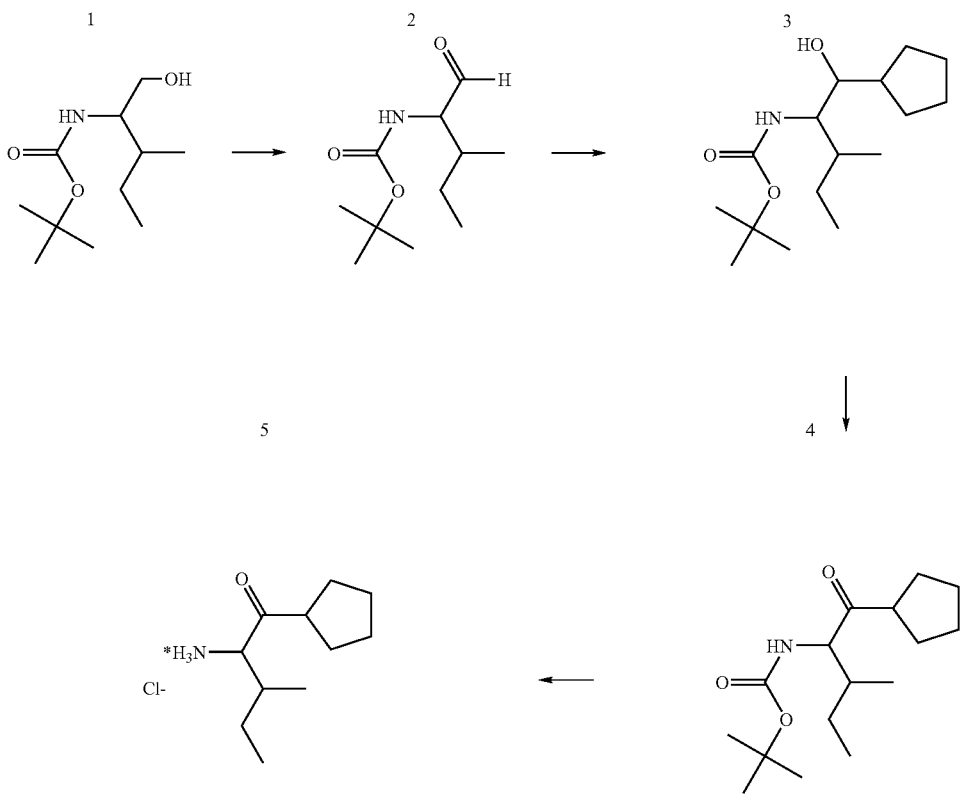

Boc-isoleucinal 2

Oxalylchloride (714 μl, 8.28 mmol) was dissolved in 10 ml of dry dichlormethane and brought to −78° C. Then DMSO (817 μl, 8.28 mmol) was added dropwise. The solution was stirred for 20 min at −78° C. Then 1 (1.00 g, 4.6 mmol) was added and the mixture was stirred for 20 min. After that TEA (2.58 ml, 18.4 mmol) was added and the mixture was allowed to reach room temperature. The mixture was diluted with hexane/ethylacetate (2/1 v/v) and 10 ml of HCl (10% in water) was added. The organic layer was separated and the aqueous phase was extracted with 20 ml of methylenechloride. All organic layers were collected and washed with brine, followed by water, then dried. The product was purified by column chromatography using silica gel and heptane/chloroform.

Yield: 0.52 g, 52% tert-butyl N-1-[cyclopentyl(hydroxy)methyl]-2-methylbutylcarbamate 3

2 (0.52 g, 2.42 mmol) was dissolved in 10 ml of dry THF and cooled down to 0° C. Then cyclopentylmagnesiumbromide (1.45 ml of a 2 M solution) was added. After completion of the reaction (2 ml) of water was added and solution was neutralized by adding aqueous HCl. Then methylenechloride was added and the organic layer was separated and dried (Na$_2$SO$_4$). After evaporation the resulting oil was used without further characterisation.

tert-butyl N-[1-(cyclopentylcarbonyl)-2-methylbutyl]carbamate 4

3 (0.61 g, 2.15 mmol) was treated like 1. Oxalylchloride (333 μl, 3.87 mmol), DMSO (382 μl, 5.37 mmol), TEA (1.2 ml, 8.59 mmol)

Yield: 0.180 g, 30%

1-cyclopentyl-3-methyl-1-oxo-2-pentanaminium chloride 5

4 (0.18 g, 0.63 mmol) was dissolved in 2 ml HCl (7 N in dioxane). After completion of the reaction the solvent was removed and the resulting oil was purified by column chromatography on silical gel using a chloroform/methanol/water gradient. The resulting oil was triturated with ether.

Yield: 0.060 g, 54%

Example 6

Synthesis of Side Chain Modified DP IV-Inhibitors 6.1 Synthesis of Boc-Glu-Thia Reaction of Boc-Glu(OMe)—OH with Thia*HCl according to Method B (see section 6.4 for methods), hydrolysis of Boc-Glu(OMe)-Thia according to Method G

6.1.1 Analytical Data for Boc-Glu-Thia

| Compound | Empirical formula $M_r$ Synthesis method Yield | MS [M + H]$^+$ TLC: $R_f$/system m.p. | $[\alpha]^{20}$D Concentration Solvent | Elemental analysis (calc./ found) % | HPLC $R_t$ [min]/system |
|---|---|---|---|---|---|
| Boc-Glu-Thia | $C_{13}H_{22}N_2O_5S$ 318.38 B + G 62% | 319.5 0.52/A$^1$ 0.42/B$^1$ 115-118° C. | −3.1 c = 1 methanol | C: 49.04/48.89 H: 6.96/6.82 N: 8.80/8.59 | 13.93/ A$^2$ |

$^1$Thin-layer chromatography
System A: chloroform/methanol 90:10
System B: benzene/acetone/acetic acid 25:10:0.5
System C: n-butanol/EA/acetic acid/$H_2O$ 1:1:1:1
$^2$HPLC separation conditions
Column: Nucleosil C-18, 7µ, 250 mm × 21 mm
Eluant: isocratic, 40% ACN/water/0.1% TFA
Flow rate: 6 ml/min
λ = 220 nm

6.2 Side Chain-Modified Boc-Glutamylthiazolidines

Boc-Glu-Thia was modified at the γ-carboxylic acid function by introducing radicals of varying size. The radicals were coupled by way of their amino group by forming an amide bond to the γ-carboxylic acid function, with a variety of coupling methods being used depending on the radical. The following amino components were attached to Boc-Glu-Thia using the method stated:

| Amino component | Coupling methods (see section 3.4) | Yields |
|---|---|---|
| Polyethylene glycol amine ($M_r \approx 8000$) | C | 93% |
| H-Gly-Gly-Gly-OH | D + E | 49% |
| H-Gly-Gly-Gly-Gly-Gly-OH | D + E | 86% |

In 2 cases, purification of the reaction products differs from the general description of synthesis.

Boc-Glu(Gly$_5$)-Thia

The product already precipitates out from the mixture on stirring overnight; it is subsequently filtered off and washed with 0.1 N HCl and copious amounts of water and then dried over $P_4O_{10}$ in vacuo.

Boc-Glu(PEG)-Thia

In contrast to the general procedure, the starting materials for the synthesis are dissolved in a 500-fold excess of DMF. After the reaction is complete, the DMF is completely removed in vacuo and the residue is dissolved in a large amount of methanol. After ether is poured on, to form an upper layer, the product precipitates out together with the unreacted PEG. Fine purification was carried out by preparative HPLC separation on a gel filtration column (Pharmazia, Sephadex G-25, 90 µm, 260 mm-100 mm).

Separating conditions: eluant: water; flow rate: 5 ml/min; λ=220 nm

6.2.2 Synthesis Data for Side Chain-Modified Boc-Glutamylthiazolidines

| Compound | Empirical formula $M_r$ Yield | MS [M + H]$^+$ TLC/$R_f$/ system m.p. | $[\alpha]^{20}$D Concentration Solvent | Elemental analysis (calc./ found) % | HPLC $R_t$ [min]/system |
|---|---|---|---|---|---|
| Boc-Glu(Gly$_3$)-Thia | $C_{19}H_{31}N_5O_8S$ 489.54 49% | 490.5 | | C: 46.62 H: 6.38 N: 14.31 | |
| Boc-Glu(Gly$_5$)-Thia | $C_{23}H_{37}N_7O_{10}S$ 603.64 86% | 604.5 0.09/C decomp. from 202° C. | n.dm. | C: 45.76/45.60 H: 6.18/6.11 N: 16.24/16.56 | 11.93/A$^2$ |
| Boc-Glu(PEG)-Thia | 93% | ≈8000 (mass emphasis) 52-53° C. | n.dm. | n.dm. | n.dm. |

$^2$HPLC separation conditions
Column: Nucleosil C-18, 7µ, 250 mm × 21 mm
Eluant: isocratic, 40% ACN/water/0.1% TFA
Flow rate: 6 ml/min
λ = 220 nm

6.3 Side Chain-Modified Glutamylthiazolidines

The N-terminal Boc protecting groups were cleaved off the compounds described in Table 3 using method F. The substances modified with Gly derivatives were purified by preparative HPLC separation and are present as trifluoroacetates. The H-Glu(PEG)-Thia was purified on a gel filtration column in the same manner as the Boc-protected precursor.

6.3.1 Synthesis Data for Side Chain-Modified Glutamylthiazolidines

| Compound | Empirical formula $M_r$ Yield | MS $[M + H]^+$ TLC/$R_f$/ system m.p. | $[\alpha]^{20}D$ Concentration Solvent | Elemental analysis (calc./ found) % | HPLC $R_t$[min]/ system |
|---|---|---|---|---|---|
| H-Glu(Gly$_3$)-Thia *TFA | $C_{16}H_{24}N_5O_8SF_3$ 503.45 94% | 503.45 0.32/C 91-94° C. | +4.1 c = 1 methanol | C: 38.17/37.56 H: 4.80/4.78 N: 13.91/13.43 | 7.84/C$^3$ |
| H-Glu(Gly$_5$)-Thia *TFA | $C_{20}H_{30}N_7O_{10}SF_3$ 617.55 98% | 617.55 0.25/C 105-107° C. | n.dm. | C: 38.90/38.82 H: 4.90/4.79 N: 15.88/15.39 | 8.22/C$^3$ |
| H-Glu(PEG)-Thia *HCl | 92% | ≈8000 (mass emphasis) | n.dm. | n.dm. | n.dm. |

$^3$HPLC separation conditions
Column: Nucleosil C-18, 7μ, 250 mm × 21 mm
Eluant: ACN/water/0.1% TFA
Gradient: 20% ACN → 90% ACN over 30 min
Flow rate: 6 ml/min
λ = 220 nm
n.dm.—not determined or not determinable

6.4 General Synthesis Procedures

Method A: Peptide Bond Attachment by the Mixed Anhydride Method Using CFIBE as Activation Reagent

10 mmol of N-terminally protected amino acid or peptide are dissolved in 20 ml of absolute THF. The solution is cooled to −15° C.±2° C. With stirring in each case, 10 mmol of N-MM and 10 mmol of chloroformic acid isobutyl ester are added in succession, the stated temperature range being strictly adhered to. After approximately 6 min, 10 mmol of the amino component is added. When the amino component is a salt, a further 10 mmol of N-MM is then added to the reaction mixture. The reaction mixture is then stirred for 2 h in the cold state and overnight at room temperature.

The reaction mixture is concentrated using a rotary evaporator, taken up in EA, washed with 5% KH$_2$SO$_4$ solution, saturated NaHCO$_3$ solution and saturated NaCl solution and dried over NaSO$_4$. After removal of the solvent in vacuo, the compound is recrystallized from EA/pentane.

Method B: Peptide Bond Attachment by the Mixed Anhydride Method Using Pivalic Acid Chloride as Activation Reagent

10 mmol of N-terminally protected amino acid or peptide are dissolved in 20 ml of absolute THF. The solution is cooled to 0° C. With stirring in each case, 10 mmol of N-MM and 10 mmol of pivalic acid chloride are added in succession, the stated temperature range being strictly adhered to. After approximately 6 min, the mixture is cooled to −15° C. and, once the lower temperature has been reached, 10 mmol of the amino component is added. When the amino component is a salt, a further 10 mmol of N-MM is then added to the reaction mixture. The reaction mixture is then stirred for 2 h in the cold state and overnight at room temperature.

Further working up is carried out as in Method A.

Method C: Peptide Bond Attachment Using TBTU as Activation Reagent

10 mmol of the N-terminally protected amino acid or peptide and 10 mmol of the C-terminally protected amino component are dissolved in 20 ml of absolute DMF. The solution is cooled to 0° C. With stirring in each case, 10 mmol of DIPEA and 10 mmol of TBTU are added in succession. The reaction mixture is stirred for one hour at 0° C. and then overnight at room temperature. The DMF is completely removed in vacuo and the product is worked up as described in Method A.

Method D: Synthesis of an Active Ester (N-hydroxysuccinimide Ester)

10 mmol of N-terminally protected amino acid or peptide and 10 mmol of N-hydroxysuccinimide are dissolved in 20 ml of absolute THF. The solution is cooled to 0° C. and 10 mmol of dicyclohexylcarbodiimide are added, with stirring. The reaction mixture is stirred for a further 2 h at 0° C. and then overnight at room temperature. The resulting N,N'-dicyclohexylurea is filtered off and the solvent is removed in vacuo and the remaining product is recrystallized from EA/pentane.

Method E: Amide Bond Attachment Using N-hydroxysuccinimide Esters

10 mmol of the C-terminally unprotected amino component is introduced into an NaHCO$_3$ solution (20 mmol in 20 ml of water). At room temperature and with stirring, 10 mmol of the N-terminally protected N-hydroxysuccinimide ester dissolved in 10 ml of dioxane are slowly added dropwise. Stirring of the reaction mixture is continued overnight and the solvent is then removed in vacuo.

Further working up is carried out as in Method A.

Method F. Cleavage of the Boc Protecting Group

3 ml of 1.1N HCl/glacial acetic acid (Method F1) or 3 ml of 1.1N HCl/dioxane (Method F2) or 3 ml of 50% TFA in DCM (Method F3) are added to 1 mmol of Boc-protected amino acid pyrrolidide, thiazolidide or peptide. The cleavage at RT is monitored by means of TLC. After the reaction is complete (approximately 2 h), the compound is precipitated out in the form of the hydrochloride using absolute diethyl ether and is isolated with suction and dried over $P_4O_{10}$ in vacuo. Using methanol/ether, the product is recrystallized or reprecipitated.

Method G: Hydrolysis 1 mmol of peptide methyl ester is dissolved in 10 ml of acetone and 11 ml of 0.1 M NaOH solution and stirred at room temperature. The course of the hydrolysis is monitored by means of TLC. After the reaction is complete, the acetone is removed in vacuo. The remaining aqueous solution is acidified, using concentrated $KH_2SO_4$ solution, until a pH of 2-3 is reached. The product is then extracted several times using EA; the combined ethyl acetate fractions are washed with saturated NaCl solution and dried over $NaSO_4$, and the solvent is removed in vacuo. Crystallization from EA/pentane is carried out.

Example 7

$K_i$-Determination

For $K_i$ determination of glutaminylpyrrolidine and glutaminylthazolidine, dipeptidyl peptidase IV from porcine kidney with a specific activity against glycylprolyl-4-nitroaniline of 37.5 U/mg and an enzyme concentration of 1.41 mg/ml in the stock solution was used.

Assay Mixture:

100 µl glutaminylpyrrolidine or glutaminylthazolidine in a concentration range of $1*10^{-5}M$-$1*10^{-7}M$ (glutaminylpyrrolidine) and $1*10^{-6}M$-$1*10^{-8}M$ (glutaminylthazolidine) respectively were admixed with 50 µl glycylprolyl-4-nitroaniline in different concentrations (0.4 mM, 0.2 mM, 0.1 mM, 0,05 mM) and 100 µl HEPES (40 mM, pH7.6; ion strength=0.125). The assay mixture was pre-incubated at 30° C. for 30 min. After pre-incubation, 20 µl DP IV (1:600 diluted) was added and measurement of yellow color development due to 4-nitroaniline release was performed at 30° C. and λ=405 nm for 10 min. using a plate reader (HTS7000 plus, Applied Biosystems, Weiterstadt, Germany).

The $K_i$-values were calculated using Graphit version 4.0.13, 4.0.13 and 4.0.15 (Erithacus Software, Ltd, UK).

7.1 Results—Ki Values of DP IV Inhibition

| Compound | Ki [M] |
| --- | --- |
| H-Asn-pyrrolidine | $1.20 * 10^{-5}$ |
| H-Asn-thiazolidine | $3.5 * 10^{-6}$ |
| H-Asp-pyrrolidine | $1.4 * 10^{-8}$ |
| H-Asp-thiazolidine | $2.9 * 10^{-6}$ |
| H-Asp(NHOH)-pyrrolidine | $1.3 * 10^{-5}$ |
| H-Asp(NHOH)-thiazolidine | $8.8 * 10^{-6}$ |
| H-Glu-pyrrolidine | $2.2 * 10^{-6}$ |
| H-Glu-thiazolidine | $6.1 * 10^{-7}$ |
| H-Glu(NHOH)-pyrrolidine | $2.8 * 10^{-6}$ |
| H-Glu(NHOH)-thiazolidine | $1.7 * 10^{-6}$ |
| H-His-pyrrolidine | $3.5 * 10^{-6}$ |
| H-His-thiazolidine | $1.8 * 10^{-6}$ |
| H-Pro-pyrrolidine | $4.1 * 10^{-6}$ |
| H-Pro-thiazolidine | $1.2 * 10^{-6}$ |
| H-Ile-azididine | $3.1 * 10^{-6}$ |
| H-Ile-pyrrolidine | $2.1 * 10^{-7}$ |
| H-L-threo-Ile-thiazolidine | $8.0 * 10^{-8}$ |
| H-L-allo-Ile-thiazolidine | $1.9 * 10^{-7}$ |
| D-threo-isoleucyl-thiazolidine-fumarate | no inhibition |
| D-allo-isoleucyl-thiazolidine-fumarate | no inhibition |
| H-L-threo-Ile-thiazolidine-succinate | $5.1 * 10^{-8}$ |
| H-L-threo-Ile-thiazolidine-tartrate | $8.3 * 10^{-8}$ |
| H-L-threo-Ile-thiazolidine-fumarate | $8.3 * 10^{-8}$ |
| H-L-threo-Ile-thiazolidine-hydrochloride | $7.2 * 10^{-8}$ |

-continued

| Compound | Ki [M] |
| --- | --- |
| H-L-threo-Ile-thiazolidine-phosphate | $1.3 * 10^{-7}$ |
| H-Val-pyrrolidine | $4.8 * 10^{-7}$ |
| H-Val-thiazolidine | $2.7 * 10^{-7}$ |
| Diprotin A | $3.45 * 10^{-6}$ |
| Diprotin B | $2.24 * 10^{-5}$ |
| Nva-Pro-Ile | $6.17 * 10^{-6}$ |
| Cha-Pro-Ile | $5.99 * 10^{-6}$ |
| Nle-Pro-Ile | $9.60 * 10^{-6}$ |
| Phe-Pro-Ile | $1.47 * 10^{-5}$ |
| Val-Pro-Val | $4.45 * 10^{-6}$ |
| Ile-Pro-Val | $5.25 * 10^{-6}$ |
| Abu-Pro-Ile | $8.75 * 10^{-6}$ |
| Ile-Pro-allo-Ile | $5.22 * 10^{-6}$ |
| Val-Pro-allo-Ile | $9.54 * 10^{-6}$ |
| Tyr-Pro-allo-Ile | $1.82 * 10^{-5}$ |
| AOA-Pro-Ile | $1.26 * 10^{-5}$ |
| t-butyl-Gly-Pro-Ile | $3.10 * 10^{-6}$ |
| Ser(Bz)-Pro-Ile | $2.16 * 10^{-5}$ |
| Aze-Pro-Ile | $2.05 * 10^{-5}$ |
| t-butyl-Gly-Pro-Val | $3.08 * 10^{-6}$ |
| Gln-Pyrr | $2.26 * 10^{-6}$ |
| Gln-Thia | $1.21 * 10^{-6}$ |
| Val-Pro-t-butyl-Gly | $1.96 * 10^{-5}$ |
| t-butyl-Gly-Pro-Gly | $1.51 * 10^{-5}$ |
| Ile-Pro-t-butyl-Gly | $1.89 * 10^{-5}$ |
| t-butyl-Gly-Pro-IleNH$_2$ | $5.60 * 10^{-6}$ |
| t-butyl-Gly-Pro-D-Val | $2.65 * 10^{-5}$ |
| t-butyl-Gly-Pro-t-butyl-Gly | $1.41 * 10^{-5}$ |
| Ile-cyclopentyl ketone | $6.29 * 10^{-6}$ |
| t-butyl-Gly-cyclohexyl ketone | $2.73 * 10^{-4}$ |
| Ile-cyclohexyl ketone | $5.68 * 10^{-5}$ |
| Val-cyclopentyl ketone | $1.31 * 10^{-5}$ |
| Val-Pro-methyl ketone | $4.76 * 10^{-8}$ |
| Val-Pro-acyloxy methyl ketone | $1.05 * 10^{-9}$ |
| Val-Pro-benzoyl methyl ketone | $5.36 * 10^{-10}$ |
| Val-Pro-benzothiazol methyl ketone | $3.73 * 10^{-8}$ |
| H-Glu-Thia | $6.2 * 10^{-7}$ |
| H-Gly(NHOH)-Thia | $1.7 * 10^{-6}$ |
| H-Glu(Gly$_3$)-Thia | $1.92 * 10^{-8}$ |
| H-Glu(Gly$_5$)-Thia | $9.93 * 10^{-8}$ |
| H-Glu(PEG)-Thia | $3.11 * 10^{-6}$ | t-butyl-Gly is defined as:

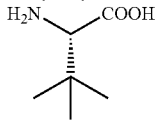

Example 8

Determination of IC$_{50}$-Values

100 µl inhibitor stock solution were mixed with 100 µl buffer (HEPES pH7.6) and 50 µl substrate (Gly-Pro-pNA, final concentration 0.4 mM) and preincubated at 30° C. Reaction was started by addition of 20 µl purified porcine DP IV. Formation of the product pNA was measured at 405 nm over 10 min using the HTS 7000Plus plate reader (Perkin Elmer) and slopes were calculated. The final inhibitor concentrations ranged between 1 mM and 30 nM. For calculation of IC50 GraFit 4.0.13 (Erithacus Software) was used.

8.1 Results—Determination of IC$_{50}$ Values

| Compound | IC50 [M] |
| --- | --- |
| Ile-thiazolidine fumarate | $1.28 * 10^{-7}$ |

-continued

| Compound | IC50 [M] |
|---|---|
| Diprotin A | 4.69 * $10^{-6}$ |
| Diprotin B | 5.54 * $10^{-5}$ |
| Phg-Pro-Ile | 1.54 * $10^{-4}$ |
| Nva-Pro-Ile | 2.49 * $10^{-5}$ |
| Cha-Pro-Ile | 2.03 * $10^{-5}$ |
| Nle-Pro-Ile | 2.19 * $10^{-5}$ |
| Ser(P)-Pro-Ile | 0.012 |
| Tyr(P)-Pro-Ile | 0.002 |
| Phe-Pro-Ile | 6.20 * $10^{-5}$ |
| Trp-Pro-Ile | 3.17 * $10^{-4}$ |
| Ser-Pro-Ile | 2.81 * $10^{-4}$ |
| Thr-Pro-Ile | 1.00 * $10^{-4}$ |
| Val-Pro-Val | 1.64 * $10^{-5}$ |
| Ile-Pro-Val | 1.52 * $10^{-5}$ |
| Abu-Pro-Ile | 3.43 * $10^{-5}$ |
| Pip-Pro-Ile | 0.100 |
| Ile-Pro-allo-Ile | 1.54 * $10^{-5}$ |
| Val-Pro-allo-Ile | 1.80 * $10^{-5}$ |
| Tyr-Pro-allo-Ile | 6.41 * $10^{-5}$ |
| AOA-Pro-Ile | 4.21 * $10^{-5}$ |
| t-butyl-Gly-Pro-Ile | 9.34 * $10^{-6}$ |
| Ser(Bz)-Pro-Ile | 6.78 * $10^{-5}$ |
| Tic-Pro-Ile | 0.001 |
| Orn-Pro-Ile | 2.16 * $10^{-4}$ |
| Gln-Thia | 5.27 * $10^{-6}$ |
| Aze-Pro-Ile | 7.28 * $10^{-5}$ |
| Ile-Hyp-Ile | 0.006 |
| t-butyl-Gly-Pro-Val | 1.38 * $10^{-5}$ |
| Gln-Pyrr | 1.50 * $10^{-5}$ |
| Val-Pro-t-butyl-Gly | 6.75 * $10^{-5}$ |
| t-butyl-Gly-Pro-Gly | 5.63 * $10^{-5}$ |
| Ile-Pro-t-butyl-Gly | 8.23 * $10^{-5}$ |
| t-butyl-Gly-Pro-IleNH$_2$ | 2.29 * $10^{-5}$ |
| t-butyl-Gly-Pro-D-Val | 1.12 * $10^{-4}$ |
| t-butyl-Gly-Pro-t-butyl-Gly | 2.45 * $10^{-5}$ |
| Aib-Pro-Ile | no inhibition |
| Ile-cyclopentyl ketone | 3.82 * $10^{-5}$ |
| t-butyl-Gly-cyclohexyl ketone | 2.73 * $10^{-4}$ |
| Ile-cyclohexyl ketone | 2.93 * $10^{-4}$ |
| Val-cyclopentyl ketone | 4.90 * $10^{-5}$ |
| Val-cyclohexyl ketone | 0.001 |
| Val-Pro-methyl ketone | 5.79 * $10^{-7}$ |
| Val-Pro-acyloxy methyl ketone | 1.02 * $10^{-8}$ |
| Val-Pro-benzoyl methyl ketone | 1.79 * $10^{-8}$ |
| Val-Pro-benzothiazol methyl ketone | 1.38 * $10^{-7}$ |

Example 9

Inhibition Of DP IV-Like Enzymes—Dipeptidyl Peptidase II

DP II (3.4.14.2) releases N-terminal dipeptides from oligopeptides if the N-terminus is not protonated (Mc-Donald, J. K., Ellis, S. & Reilly, T. J., 1966, *J. Biol. Chem.*, 241, 1494-1501). Pro and Ala in P$_1$-position are preferred residues. The enzyme activity is described as DP IV-like activity, but DP II has an acidic pH-optimum. The enzyme used was purified from porcine kidney.

Assay:

100 µl glutaminylpyrrolidine or glutaminylthazolidine in an concentration range of 1*$10^{-4}$ M-5*$10^{-8}$ M were admixed with 100 µl µl buffer solution (40 mM HEPES, pH7.6, 0.015% Brij, 1 mM DTT), 50 µl lysylalanylaminomethylcoumarine solution (5 mM) and 20 µl porcine DP II (250fold diluted in buffer solution). Fluorescence measurement was performed at 30° C. and $\lambda_{exiatation}$=380 nm, $\lambda_{emission}$=465 nm for 25 min using a plate reader (HTS7000plus, Applied Biosystems, Weiterstadt, Germany). The K$_i$-values were calculated using Graphit 4.0.15 (Erithacus Software, Ltd., UK) and were determined as K$_i$=8.52*$10^{-5}$ M±6.33*$10^{-6}$ M for glutaminylpyrrolidine and K$_i$=1.07*$10^{-5}$ M±3.81*$10^{-7}$ M for glutaminylthazolidine. Both compounds act as non-competitive type inhibitors against porcine DP II.

Example 10

Cross Reacting Enzymes

Glutaminylpyrrolidine or glutaminylthazolidine were tested for their cross reacting potency against dipeptidyl peptidase I, prolyl oligopeptidase and dipeptidyl peptidase II.

Dipeptidyl Peptidase I (DP I, Cathepsin C):

DP I or cathepsin C is a lysosomal cysteine protease which cleaves off dipeptides from the N-terminus of their substrates (Gutman, H. R. & Fruton, J. S., 1948, *J. Biol. Chem.*, 174, 851-858). It is classified as a cysteine protease. The enzyme used was purchased from Qiagen (Qiagen GmbH, Hilden, Germany). In order to get a fully active enzyme, the enzyme was diluted 1000 fold in MES buffer pH5,6 (40 mM MES, 4 mM DTT, 4 mM KCl, 2 mM EDTA, 0.015% Brij) and pre-incubated for 30 min at 30° C.

Assay:

50 µl glutaminylpyrrolidine or glutaminylthazolidine in a concentration range of 1*$10^{-5}$M-1*$10^{-7}$M were admixed with 110 µl buffer-enzyme-mixture. The assay mixture was pre-incubated at 30° C. for 15 min. After pre-incubation, 100 µl, histidylseryl-β-nitroaniline (2*$10^{-5}$M) was added and measurement of yellow color development due to β-nitroaniline release was performed at 30° C. and $\lambda_{excitation}$=380 nm, $\lambda_{emission}$=465 nm for 10 min., using a plate reader (HTS7000 plus, Applied Biosystems, Weiterstadt, Germany).

The IC 50-values were calculated using Graphit 4.0.15 (Erithacus Software, Ltd., UK). No inhibition of the DP I enzyme activity by glutaminylpyrrolidine or glutaminylthazolidine was found.

Prolyl Oligopeptidase (POP)

Prolyl oligopeptidase (EC 3.4.21.26) is a serine type endoprotease which cleaves off peptides at the N-terminal part of the Xaa-Pro bond (Walter, R., Shlank, H., Glass, J. D., Schwartz, I. L. & Kerenyi, T. D., 1971, *Science*, 173, 827-829). Substrates are peptides with a molecular weight up to 3000 Da. The enzyme used was a recombinant human prolyl oligopeptidase. Recombinant expression was performed in *E. coli* under standard conditions as described elsewhere in the state of the art.

Assay:

100 µl glutaminylpyrrolidine or glutaminylthazolidine in an concentration range of 1*$10^{-4}$M-5*$10^{-8}$M were admixed with 100 µl µl buffer solution (40 mM HEPES, pH7.6, 0.015% Brij, 1 mM DTT) and 20 µl POP solution. The assay mixture was pre-incubated at 30° C. for 15 min. After pre-incubation, 50 µl glycylprolylprolyl-4-nitroaniline solution (0.29 mM) was added and measurement of yellow color development due to 4-nitroaniline release was performed at 30° C. and λ=405 nm for 10 min using a plate reader (sunrise, Tecan, Crailsheim, Germany). The IC 50-values were calculated using Graphit 4.0.15 (Erithacus Software, Ltd., UK). No inhibition of POP activity by glutaminylpyrrolidine or glutaminylthazolidine was found.

Prolidase (X-Pro Dipeptidase)

Prolidase (EC 3.4.13.9) was first described by Bergmann & Fruton (Bergmann, M. & Fruton, J S, 1937, *J. Biol. Chem.* 189-202). Prolidase releases the N-terminal amino acid from Xaa-Pro dipeptides and has a pH optimum between 6 and 9.

Prolidase from porcine kidney (ICN Biomedicals, Eschwege, Germany). was solved (1 mg/ml) in assay buffer (20 mM NH$_4$(CH$_3$COO)$_2$, 3 mM MnCl$_2$, pH 7.6). In order to get a fully active enzyme the solution was incubated for 60 min at room temperature.

Assay:

450 µl glutaminylpyrrolidine or glutaminylthazolidine in an concentration range of $5*10^{-3}$ M-$5*10^{-7}$ M were admixed with 500 µl buffer solution (20 mM NH$_4$(CH$_3$COO)$_2$, pH 7.6) and 250 µl Ile-Pro-OH (0.5 mM in the assay mixture). The assay mixture was pre-incubated at 30° C. for 5 min. After pre-incubation, 75 µl Prolidase (1:10 diluted in assay buffer) were added and measurement was performed at 30° C. and λ=220 nm for 20 min using a UV/Vis photometer, UV1 (Thermo Spectronic, Cambridge, UK).

The IC 50-values were calculated using Graphit 4.0.15 (Erithacus Software, Ltd., UK). They were determined as IC 50>3 mM for glutaminylthiazolidine and as IC 50=$3.4*10^{-4}$ M±$5.63*10^{-5}$ for glutaminylpyrrolidine.

Example 11

Determination of DP IV Inhibiting Activity After Intravasal and Oral Administration to Wistar Rats Animals Male Wistar rats (Shoe: Wist(Sho)) with a body weight ranging between 250 and 350 g were purchased from Tierzucht Schönwalde (Schönwalde, Germany).

Housing Conditions

Animals were single-caged under conventional conditions with controlled temperature (22±2° C.) on a 12/12 hours light/dark cycle (light on at 06:00 AM). Standard pelleted chow (ssniff® Soest, Germany) and tap water acidified with HCl were allowed ad libitum.

Catheter Insertion into Carotid Artery

After ≧one week of adaptation at the housing conditions, catheters were implanted into the carotid artery of Wistar rats under general anaesthesia (i.p. injection of 0.25 ml/kg b.w. Rompun® [2%], BayerVital, Germany and 0.5 ml/kg b.w. Ketamin 10, Atarost GmbH & Co., Twistringen, Germany). The animals were allowed to recover for one week. The catheters were flushed with heparin-saline (100 IU/ml) three times per week. In case of catheter dysfunction, a second catheter was inserted into the contra-lateral carotid artery of the respective rat. After one week of recovery from surgery, this animal was reintegrated into the study. In case of dysfunction of the second catheter, the animal was withdrawn from the study. A new animal was recruited and the experiments were continued in the planned sequence, beginning at least 7 days after catheter implantation.

Experimental Design

Rats with intact catheter function were administered placebo (1 ml saline, 0.154 mol/l) or test compound via the oral and the intra-vasal (intra-arterial) route.

After overnight fasting, 100 µl samples of heparinised arterial blood were collected at −30, −5, and 0 min. The test substance was dissolved freshly in 1.0 ml saline (0.154 mol/l) and was administered at 0 min either orally via a feeding tube (75 mm; Fine Science Tools, Heidelberg, Germany) or via the intra-vasal route. In the case of oral administration, an additional volume of 1 ml saline was injected into the arterial catheter. In the case of intra-arterial administration, the catheter was immediately flushed with 30 µl saline and an additional 1 ml of saline was given orally via the feeding tube.

After application of placebo or the test substances, arterial blood samples were taken at 2.5, 5, 7.5, 10, 15, 20, 40, 60 and 120 min from the carotid catheter of the conscious unrestrained rats. All blood samples were collected into ice cooled Eppendorf tubes (Eppendorf-Netheler-Hinz, Hamburg, Germany) filled with 10 µl 1 M sodium citrate buffer (pH 3.0) for plasma DP IV activity measurement. Eppendorf tubes were centrifuged immediately (12000 rpm for 2 min, Hettich Zentrifuge EBA 12, Tuttlingen; Germany): The plasma fractions were stored on ice until analysis or were frozen at −20° C. until analysis. All plasma samples were labelled with the following data:

Code number
Animal Number
Date of sampling
Time of sampling

Analytical Methods

The assay mixture for determination of plasma DP IV activity consisted of 80 µl reagent and 20 µl plasma sample. Kinetic measurement of the formation of the yellow product 4-nitroaniline from the substrate glycylprolyl-4-nitroaniline was performed at 390 nm for 1 min at 30° C. after 2 min pre-incubation at the same temperature. The DP IV activity was expressed in mU/ml.

Statistical Methods

Statistical evaluations and graphics were performed with PRISM® 3.02 (GraphPad Software, Inc.). All parameters were analysed in a descriptive manner including mean and SD.

11.1 Results—in vivo DP IV-Inhibition at $t_{max}$

| STRUCTURE | Dose (mg/kg) | i.v. (%) | p.o. (%) |
|---|---|---|---|
| Gln-Pyrr | 100 | 80 | 67 |
| Gln-Thia | 100 | 88 | 71 |
| Diprotin A | 100 | 73 | no inhibition |
| Diprotin B | 100 | 50 | no inhibition |
| Tyr(P)-Pro-Ile | 100 | 37 | no inhibition |
| tBuGly-Pro-Ile | 100 | 71 | 28 |
| tButGly-Pro-Val | 100 | 72 | 25 |
| Ala-Val-Pro-Acyloxymethylketone | 100 | 89 | 86 |
| Ala-Val-Pro-Benzoyl-methylketone | 100 | 97 | 76 |
| Ile-cyclopentyl-ketone | 100 | 34 | 15 |

Example 12

Action of Side Chain-Modified Glutamylthiazolidines as Non-Readily-Transportable DP IV-Inhibitors Side chain-modified glutamylthiazolidines having a structure H-Glu(X)-Thia were synthesised, with polyethylene glycol or glycine oligomers of various chain lengths being used as X (see Method A of example for description of synthesis). The binding characteristics of those derivatives and their transportability by the peptide transporter PepT1 were investigated.

Surprisingly, it was found that the side chain modifications alter the binding characteristics of the compounds to DP IV only to a slight extent. In contrast, the ability of the inhibitors to be transported by the peptide transporter is dramatically diminished by the side chain modification.

Inhibitors of DP IV or DP IV-like enzymes are therefore well suited to achieving site directed inhibition of DP IV in the body.

12.1 Results: Transportability of Selected DP IV-Inhibitors.

| Compound | EC50 (mM)[1] | $I_{max}$ (nA)[2] |
|---|---|---|
| amino acid thiazolidides | | |
| H-Ile-Thia | 0.98 | 25 ± 8 |
| H-Glu-Thia | 1.1 | 35 ± 13 |
| side chain-modified glutamylthiazolidines | | |
| H-Gly(NHOH)-Thia | 3.18 | 42 ± 11 |
| H-Glu(Gly$_3$)-Thia | 8.54 | n.d.[3] |
| H-Glu(Gly$_5$)-Thia | >10 | n.d.[3] |
| H-Glu(PEG)-Thia | >10 | n.d.[3] |

[1]Effective concentrations of the compounds inhibiting the binding of [3]H-D-Phe-Ala (80 mM) to PepT1-expressing P. pastoris cells by 50% ($EC_{50}$ values)
[2]Transport characteristics at PepT1-expressing oocytes of X. leavis - by means of two-electrode voltage clamp method, I = inward currents generated by the transport Example 13

Efficacy of Dipeptidyl-Peptidase IV (DPIV; CD26) Inhibitors Conjugated with Specific Careers for the Neuronal Targeting in Models for Multiple Sclerosis 13.1 Experiment 1: i.p. Treatment (0-30 mg/kg b.w. Isoleucyl Thiazolidine Fumarate/Day) from Day 1-15. Scores Until Day 15 p.i.

Materials and Methods

Animals

For the first experiment female inbred Lewis rats (n=50) with a mean body weight of 190±6 g, were obtained from Charles River (Bad Sulzfeld, Germany). Animals were randomly assigned to the different experimental conditions. Rats were housed four per cage under a 12:12 h light: dark cycle (lights off at 18:00 h) and at constant temperature (24° C.) in a specific pathogen free air-conditioned colony room with food (Altromin lab chow pellets) and tap water available ad lib. The animals underwent routine cage maintenance once a week. All research and animal care procedures were approved by the government of Lower Saxony in Hannover, Germany, and performed in compliance with international animal welfare standards.

Induction of EAE

Guinea pig MBP (50 μg/rat) was emulsified in Complete Freund's adjuvant (CFA) containing heat-killed *Mycobacterium tuberculosis* (H37Ra; 225 μg/rat) and injected s.c. at the base of the tail in a total volume of 100 μl (12). CFA (Sigma) and heat-killed *Mycobacterium tuberculosis* (H37Ra) were purchased from Life Technologies, Inc. (Rockville, Md.). Clinical disease was scored on the following scale: 0.5: partial loss of tail tone; 1.0: complete tail atony; 2.0: hind limb weakness; 2.5: hind limb paralysis of one leg; 3.0: hind limb paralysis of both legs; 3.5: limb paralysis of three legs; 4.0: quadriplegia and moribund status; 5.0: death due to EAE. Experiments were terminated on day 15 post immunization when most of the animals were about 48 h after maximal clinical score. The incidence of adjuvant-induced arthritis was remarkably low (n=0 in the 1$^{st}$ experiment) using the base of the tail as an immunization site. In general, animals exhibiting signs of arthritis or not developing any signs of EAE or showing signs of peritonitis on autopsy were excluded from further analysis. In the first experiment no signs of arthritis and no sudden deaths and/or peritonitis due to repeated ip-injection were found. Two animals in the 1 mg/kg-treatment-group did not develop clear signs of EAE (score>1) and therefore were exclude from further analysis although this eventually might reflect a treatment effect. Immunization at the base of tail might cause acute inflammation, which in turn might affect the tone of the tail during the first days post immunization.

The first experiment out of five was conducted in phase 1:

Overall-Effect:

Statistical Analysis

Comparison over time between the clinical course of EAE of the different treatment conditions was conducted using a two factorial analysis of variance (ANOVA) for repeated measures. Sums of clinical scores of EAE, onset and peak of disease were calculated on the basis of the clinical scores per day and analyzed using a one factorial ANOVA and post hoc Fisher's PLSD tests, if appropriate. All data are presented as means±SEM.

Results

Effect of daily injections of isoleucyl thiazolidine fumarate on clinical course of EAE in Lewis rats The clinical course of the EAE is illustrated in FIG. 1. Two factor ANOVA for repeated measures (treatment×clinical scores over time) revealed a significant interaction of the two factors ($F(4,56)=1.7$; $p=0.001$) indicating a differential course of the disease. This interaction is most probably due to the fact that inhibitor treatment aggravated the initial course of EAE while it improved recovery from disease.

Separate one factor ANOVAs split by day revealed significant (day 11: $F(4,43)=2.8$; $p<0.05$; day 12: $F(4,43)=3.0$; $p<0.05$) disease-aggravating effects at the 1 mg dosage on days 11 and 12 post immunization (p.i.), while the 10 mg dose significantly ($F(4,43)=4.8$; $p<0.001$) reduced clinical score at day 15 p.i. This again indicates that the inhibitor initially tends to aggravate the disease while at later stages it results in an accelerated recovery from disease. Further analysis of key parameter derived from the clinical course demonstrated that inhibitor treatment at the 10 mg/kg dosage shortened the latency until onset of disease for about 1 day.

Conclusion

Daily intraperitoneal treatment with the DPIV-Inhibitor isoleucyl thiazolidine fumarate over a wide range of dosages in Lewis rats for a period of 15 days post immunization with MBP in CFA showed that the drug initially aggravates and during recovery phase improves the clinical course of the disease. It is possible that initial pro-inflammatory effects during acute disease may switch into anti-inflammatory or other clinics improving effects after reaching peak of disease. These late effects may overall be beneficial. Further experiments will test this hypothesis by comparing "early" vs. "late" or "induction" vs. "ongoing" disease effects.

13.2 Experiment 2: i.p. Treatment (0-30 mg/kg b.w. Isoleucyl Thiazolidine Fumarate/Day) from Day 5-15. Scores Until Day 21 p.i.

Materials and Methods

Animals

For the second experiment, male inbred Lewis rats (n=50) with a mean body weight of 230±12 g, were obtained from Charles River (Bad Sulzfeld, Germany). Animals were randomly assigned to the different experimental conditions. Rats were housed four per cage under a 12:12 h light: dark cycle (lights off at 18:00 h) and at constant temperature (24° C.) in a specific pathogen free air-conditioned colony room with food (Altromin lab chow pellets) and tap water available ad lib. The animals underwent routine cage maintenance once a week.

Induction of EAE

Guinea pig MBP (50 μg/rat) was emulsified in Complete Freund's adjuvant (CFA) containing heat-killed *Mycobacterium tuberculosis* (H37Ra; 225 μg/rat) and injected s.c. at the base of the tail in a total volume of 100 μl (12). CFA (Sigma) and heat-killed *Mycobacterium tuberculosis* (H37Ra) were purchased from Life Technologies, Inc. (Rockville, Md.). Clinical disease was scored on the following scale: 0.5: partial loss of tail tone; 1.0: complete tail atony; 2.0: hind limb weakness; 2.5: hind limb paralysis of one leg; 3.0: hind limb paralysis of both legs; 3.5: limb paralysis of three legs; 4.0: quadriplegia and moribund status; 5.0: death due to EAE. Experiments were terminated on day 21 post immunization (p.i.).

General Observations During EAE in the Second Experiment

The incidence of adjuvant-induced arthritis was remarkably low (n=0 in the $2^{nd}$ experiment) using the base of the tail as an immunization site. In the second experiment no signs of arthritis were found. Surprisingly, and similar in comparison with the first experiment, four animals in the 1 mg/kg-treatment-group did not develop clear signs of EAE (score>1). This time, these animals remained in the analysis, because this finding is probably due to the treatment. In this experiment a phenomenon called "disease dissociation" was observed. In several animals there was a clear tonus of the tail associated with a clear weakness of the hind limbs. The animals were scored maximal, i.e. 2.

Statistical Analysis

Comparison over time between the clinical course of EAE of the different treatment conditions was conducted using a two factorial analysis of variance (ANOVA) for repeated measures. Sums of clinical scores of EAE, onset and peak of disease were calculated on the basis of the clinical scores per day and analyzed using a one factorial ANOVA and post hoc Fisher's PLSD tests, if appropriate. All data are presented as means±SEM.

Results

Figure 3:
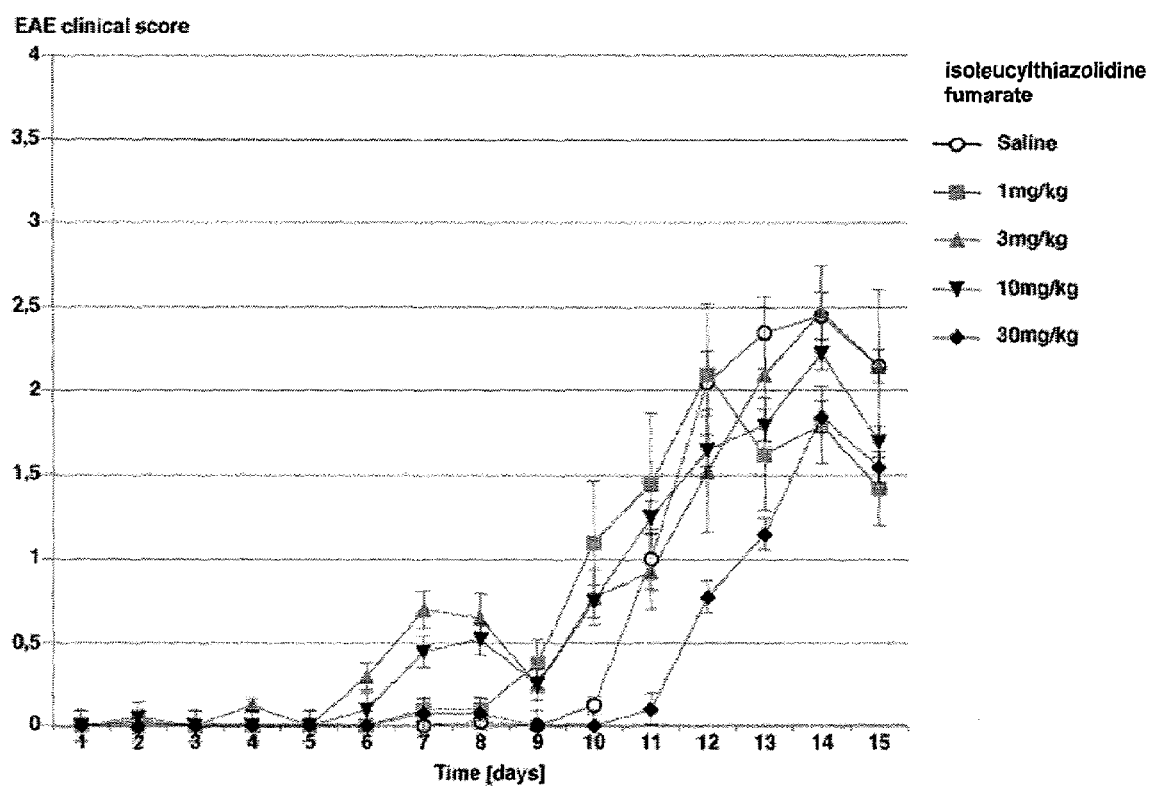
FIG. 3: Illustrates the clinical course of experimental autoimmune encephalomyelitis (EAE). The effects of different dosages of isoleucyl thiazolidine fumarate during ongoing disease (days 5-15 p.i.) on the clinical course of EAE in adult male Lewis rats were studied. Symbols represent means±SEM of the mean clinical score per day. Two factor ANOVA for repeated measures revealed significant main effects for the factor treatment and a significant interaction between the factors "treatment" and "clinical score over time" indicating that treatment significantly modulated the course of the disease and furthermore indicating that the different dosage act differentially. After initiation of treatment moderate dosages act proinflammatory and cause an "early peak" or aggravation of disease. During the acute phase of the disease between day 9-13, high dose of isoleucyl thiazolidine fumarate clearly improved the clinical course (scoring is at present continued until day 21 p.i.).
Figure 4:
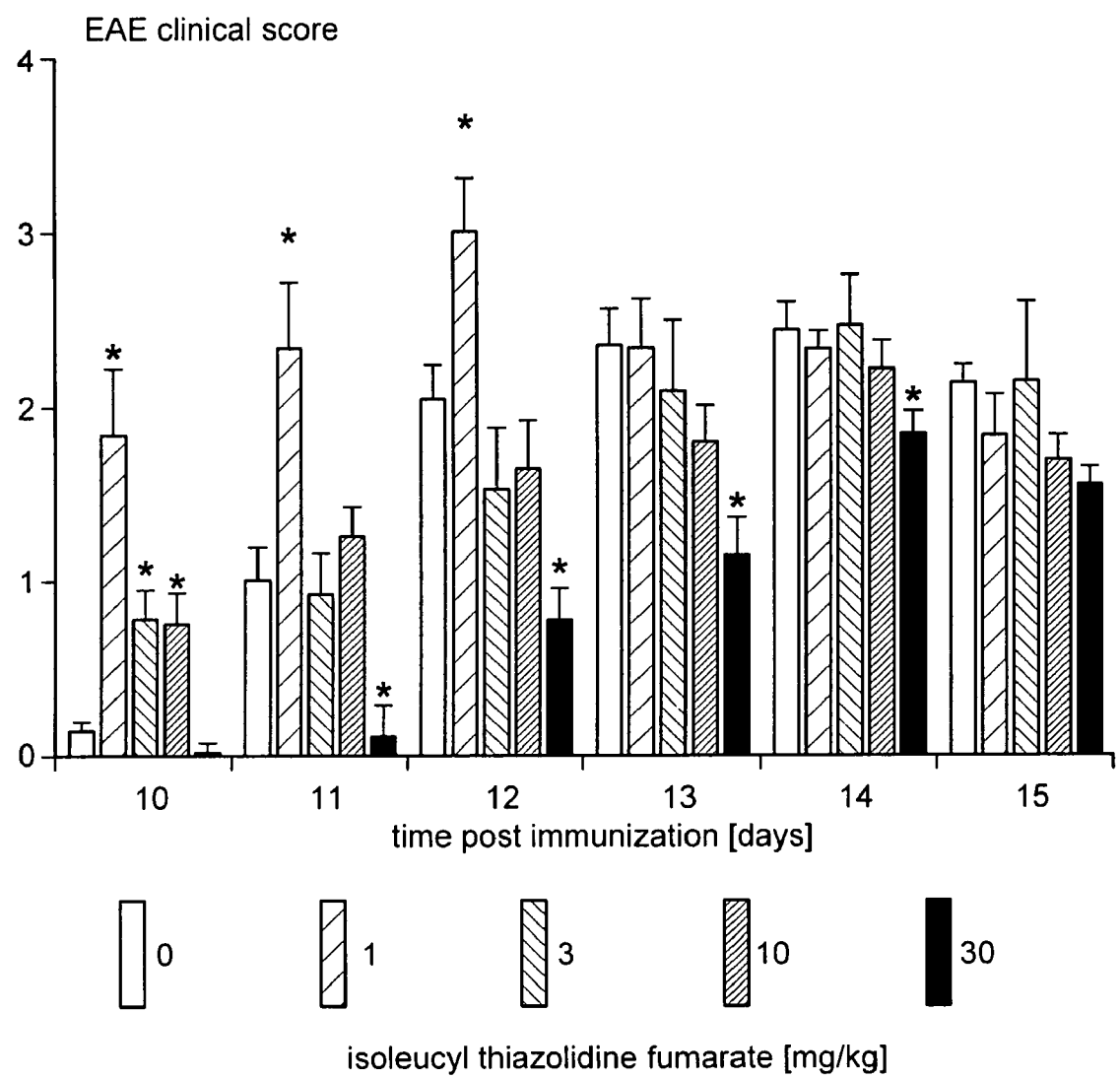
FIG. 4: Illustrates the clinical course of experimental autoimmune encephalomyelitis (EAE) in isoleucyl thiazolidine fumarate treated rats split by days 10-15 post immunization. Separate one factor ANOVAs revealed significant disease-aggravating effect at the 1 mg dosage on day 11 and 12 p.i., while the 10 mg dose significantly reduced clinical score at day 15 p.i. This indicates that the inhibitor initially tends to aggravate the disease while at later stages it results in an accelerated recovery from disease. Columns represent means±SEM of the mean clinical score per day. Asterisks indicate significant post-hoc effects in the PLSD test with *<0.05 and **<0.001.

Effect of Daily Injections of Isoleucyl Thiazolidine Fumarate During Ongoing EAE in Male Lewis Rats The clinical course of the EAE is illustrated in FIG. 3. Two factor ANOVA for repeated measures (treatment×clinical scores over time) revealed a significant effect for the factor treatment ($F(4,45)=4.3$; $p=0.0048$) and a significant interaction of the two factors ($F(4,45)=3.5$; $p<0.0001$) indicating a differential course of the disease. This interaction is most probably due to the fact that low dose inhibitor treatment aggravated or even "induced" an early peak in the initial course of EAE while high dose improved cleary inhibited the acute phase of the disease. Separate one factor ANOVAs split by day revealed significant disease aggravating effects in two peak of the disease. The 3 mg and 10 mg dosages induced a significant first peak of disease activity directly after initiation of treatment on days 6-9 (see FIG. 3; day 6: $F(4,41)=6.7$; $p=0.0003$; day 7: $F(4,41)=13.4$; $p<0.0001$; day 8: $F(4,41)=10.0$; $p<0.0001$; day 9: $F(4,41)=6.0$; $p=0.0007$). In the second peak, the "classical acute EAE", which was more severe than the first one, the 1 mg dose aggravate the clinical scores while the high dosage of 30 mg/kg exerted significant delaying and ameliorating effects (see FIG. 4; day 10: $F(4,41)=16$; $p<0.0001$; day 11: $F(4,41)=13.5$; $p<0.0001$; day 12: $F(4,41)=8.0$; $p<0.0001$; day 13: $F(4,43)=3.4$; $p=0.017$). This indicates proinflammatory effects of low dose inhibitor treatment while high dose inhibitior acts protective or anti-inflammatory-like in this model of MS. Further analysis of key parameter derived from the clinical course demonstrated that inhibitor treatment at the 1 mg/kg dosage exerts pro-inflammatory effects while 30 mg/kg mediated protective-like or anti-inflammatory effects with a delay in the onset.

| | Clinical scores of EAE in male Lewis rats treated from days 5-15(21) p.i. | | | | |
|---|---|---|---|---|---|
| | isoleucyl thiazolidine fumarate | | | | |
| Scores | 0 mg/kg | 1 mg/kg | 3 mg/kg | 10 mg/kg | 30 mg/kg |
| Onset of disease (1st day of score > 1) | 11.8 | 10.3* | 12.0 | 12.1 | 14.0*** |
| Maximal score | 2.6 | 2.8 | 3.0 | 2.1 | 2.0* |
| Sum of scores | 10.2 | 14.2* | 12.0 | 10.8 | 5.6** |
| Average score | 0.68 | 0.96* | 0.8 | 0.72 | 0.37** |

The various key parameters derived from EAE scores significantly differ in rats treated with different dosages of isoleucyl thiazolidine fumarate from days 5-15. Proinflammatory effects of 1 mg and anti-inflammatory effects of 30 mg/kg are evident. Data represent means.
*$p < 0.05$,
**$p < 0.01$,
***$p < 0.0001$ vs. control.

Conclusion

This experiment investigated the effects of daily intraperitoneal treatment with the DPIV-Inhibitor isoleucyl thiazolidine fumarate over a wide range of dosages in male Lewis rats for 10 days with the treatment being initiated at day 5 post immunization with MBP in CFA. Treatment caused a significant dose-dependent and bimodal treatment effects in this design and model for MS. Low dose (1 mg) of the drug initially aggravates the acute phase of EAE. Moderate dose of isoleucyl thiazolidine fumarate (3 and 10 mg) induces an early "first peak" of disease directly after initiation of disease, suggestive for direct pro-inflammatory effects in vivo. High dose of the drug (30 mg) exerts clearly a potent anti-inflammatory effect and a delay in the onset of disease. The so-called proinflammatory effects are not clear in their relevance for this model. Since treatment and scoring is continued, effects of the recovery phase of the disease are still to be expected.

What is claimed is:

1. A method for treating multiple sclerosis, the method comprising administering to a subject in need thereof, a pharmaceutical composition comprising a pharmaceutically acceptable carrier or diluent and a therapeutically effective amount of at least one inhibitor of dipeptidyl peptidase IV of formula

or a stereoisomer or pharmaceutically acceptable salt thereof,
wherein
A is glutamic acid;
B is Gly$_n$, wherein n is from 1 to 6, and B is covalently bound to at least one functional group in the side chain of A; and
C is a thiazolidine, pyrrolidine, cyanopyrrolidine, hydroxyproline, dehydroproline or piperidine group amide-bonded to A.

2. The method of claim 1, wherein C is thiazolidine or pyrrolidine.

3. The method of claim 2, wherein C is thiazolidine.

4. The method of claim 2, wherein C is pyrrolidine.

5. The method of claim 1, wherein n is 3.

6. The method of claim 1, wherein n is 5.

7. The method of claim 1 wherein the at least one inhibitor of dipeptidyl peptidase IV is capable of inhibiting activity of dipeptidyl peptidase IV by at least 10%.

8. The method of claim 7 wherein the at least one inhibitor of dipeptidyl peptidase IV is capable of inhibiting activity of dipeptidyl peptidase IV by at least 40%.

9. The method of claim 8 wherein the at least one inhibitor of dipeptidyl peptidase IV is capable of inhibiting activity of dipeptidyl peptidase IV by at least 60%.

10. The method of claim 9 wherein the at least one inhibitor of dipeptidyl peptidase IV is capable of inhibiting activity of dipeptidyl peptidase IV by at least 70%.

11. The method of claim 1 wherein the at least one inhibitor of dipeptidyl peptidase IV is substantially incapable of being transported by the peptide transporter PepT1.

12. A method for treating multiple sclerosis, the method comprising administering to a subject in need thereof, a pharmaceutical composition comprising a pharmaceutically acceptable carrier or diluent and a therapeutically effective amount of at least one inhibitor of dipeptidyl peptidase IV, or a stereoisomer or pharmaceutically acceptable salt thereof, wherein the at least one inhibitor of dipeptidyl peptidase IV is selected from the group consisting of Glu(Gly$_3$)-Thia, Glu(Gly$_5$)-Thia and Glu(PEG)-Thia.

13. A method for treating multiple sclerosis, the method comprising administering to a subject in need thereof, a pharmaceutical composition comprising a pharmaceutically acceptable carrier or diluent and a therapeutically effective amount of at least one inhibitor of dipeptidyl peptidase IV of formula

or a stereoisomer or pharmaceutically acceptable salt thereof,
wherein
A is an amino acid having a side chain with at least one functional group;
B comprises Gly$_n$, wherein n is from 1 to 6, and B is covalently bound to at least one functional group in the side chain of A; and
C is a thiazolidine, pyrrolidine, cyanopyrrolidine, hydroxyproline, dehydroproline or piperidine group amide-bonded to A.

* * * * *